(12) United States Patent  
Williams

(10) Patent No.: US 9,434,126 B1  
(45) Date of Patent: Sep. 6, 2016

(54) ODOR ABSORBING AND CONTROLLING DEVICE

(71) Applicant: Erwin B. Williams, Columbia, SC (US)

(72) Inventor: Erwin B. Williams, Columbia, SC (US)

( * ) Notice: Subject to any disclaimer, the term of this patent is extended or adjusted under 35 U.S.C. 154(b) by 0 days.

(21) Appl. No.: 14/982,779

(22) Filed: Dec. 29, 2015

Related U.S. Application Data

(63) Continuation-in-part of application No. 14/452,414, filed on Aug. 5, 2014, now abandoned.

(60) Provisional application No. 61/862,160, filed on Aug. 5, 2013.

(51) Int. Cl.
| | |
|---|---|
| *B32B 7/00* | (2006.01) |
| *B32B 3/04* | (2006.01) |
| *B32B 5/02* | (2006.01) |
| *B32B 5/24* | (2006.01) |
| *A47G 9/00* | (2006.01) |
| *A47G 9/02* | (2006.01) |
| *A47C 27/14* | (2006.01) |
| *A61F 13/84* | (2006.01) |

(52) U.S. Cl.
CPC ............... *B32B 3/04* (2013.01); *A47C 27/142* (2013.01); *A47G 9/007* (2013.01); *A47G 9/0223* (2013.01); *A61F 13/8405* (2013.01); *B32B 5/024* (2013.01); *B32B 5/245* (2013.01); *A61F 2013/842* (2013.01); *A61F 2013/8408* (2013.01); *B32B 2262/106* (2013.01); *B32B 2264/108* (2013.01); *B32B 2307/758* (2013.01); *B32B 2437/00* (2013.01); *B32B 2601/00* (2013.01)

(58) Field of Classification Search
CPC ............................... B32B 5/26; H01L 23/293
USPC ............................................................ 428/76
See application file for complete search history.

(56) References Cited

U.S. PATENT DOCUMENTS

| | | |
|---|---|---|
| 3,101,488 A | 8/1963 | Peebles |
| 4,928,681 A | 5/1990 | Langston et al. |
| 5,665,081 A | 9/1997 | Grosse |
| 6,245,697 B1 | 6/2001 | Conrad et al. |
| 6,313,371 B1 | 11/2001 | Conant et al. |
| 6,578,910 B2 | 6/2003 | Andersson et al. |
| 6,926,862 B2 | 8/2005 | Fontenot et al. |
| 7,559,610 B1 | 7/2009 | Hong Min |
| 2005/0015882 A1 | 1/2005 | Huza |
| 2006/0200910 A1* | 9/2006 | Taylor ................... A47C 7/021 5/652 |
| 2013/0045252 A1 | 2/2013 | Rawlings et al. |

FOREIGN PATENT DOCUMENTS

KR 20120110772 10/2012

\* cited by examiner

*Primary Examiner* — Brent O'Hern
(74) *Attorney, Agent, or Firm* — P. Jeff Martin; The Law Firm of P. Jeffrey Martin, LLC

(57) ABSTRACT

An odor controlling device includes a panel structure to which an adjustable holding component is detachably secured. The panel structure includes at least one layer. The at least one layer includes double woven activated charcoal fiber cloth. The panel structure may have another layer which includes a flexible foam material positioned below the charcoal fiber cloth. The foam material may be incorporated with a suitable and effective odor absorbing, neutralizing, controlling, removing and/or adsorbing material.

13 Claims, 27 Drawing Sheets

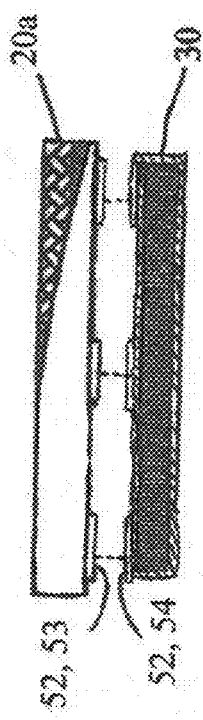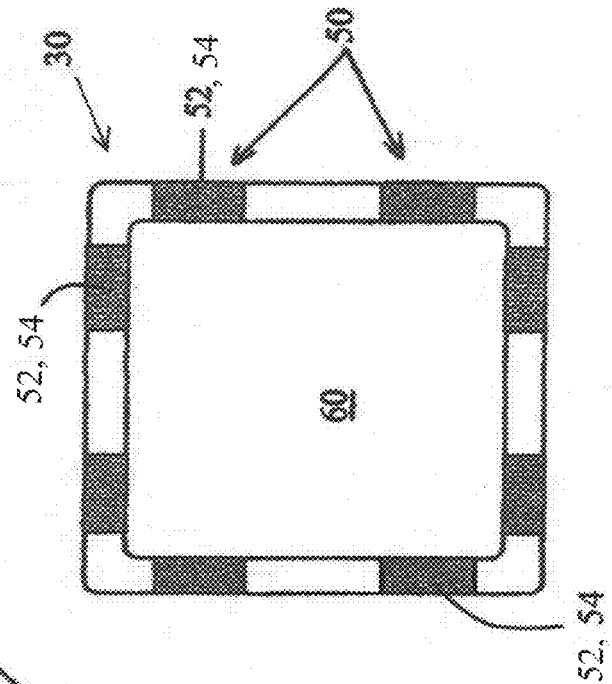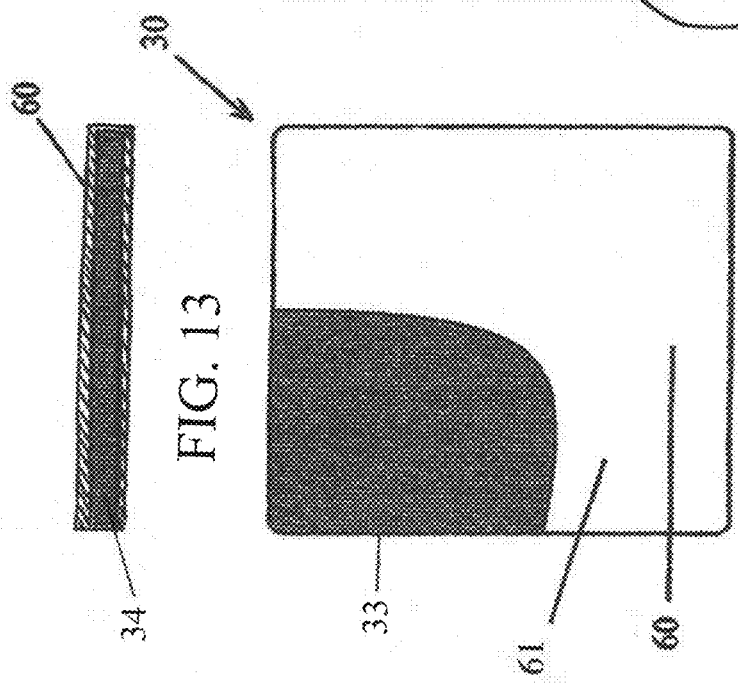

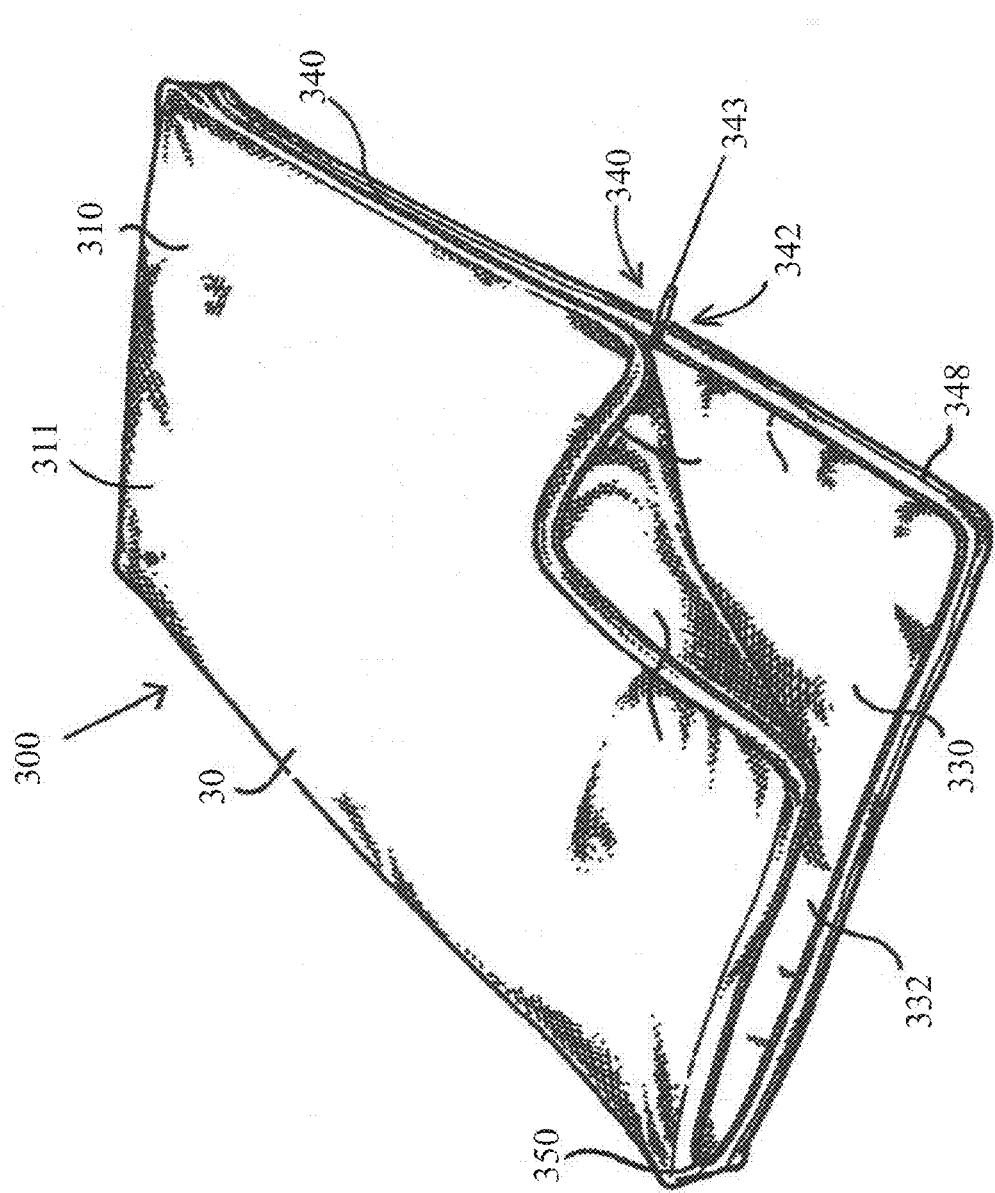

ODOR ABSORBING AND CONTROLLING DEVICE

RELATED APPLICATIONS

The present application is a Continuation-in-Part of application Ser. No. 14/452,414, filed on Aug. 5, 2014, which claims the benefit of priority to U.S. Provisional Patent Application No. 61/862,160 filed on Aug. 5, 2013, the entire contents both of which is incorporated herein by reference.

BACKGROUND OF THE INVENTION

1. Field of the Invention

The present invention relates generally to odor absorbent pads, and more particularly, to an odor absorbing and controlling device.

2. Description of the Related Art

Currently there exist in the art various odor absorbing sanitary pads, absorbent liners, ventilation devices for bedding, and seat constructions incorporated with means for removing odors. However, the prior art has failed to disclose or teach an odor absorbing and controlling device adapted for use as a seat cushion, seat back rest or back support, and odor absorbing and controlling bedding and mattress support, and which includes a top panel structure releasably attachable to a bottom panel structure, the top panel structure and bottom panel structure each comprises a suitable and effective odor absorbing, neutralizing, controlling, removing and/or adsorbing material.

Accordingly, a need exists for an odor absorbing and controlling device which provides the novel combination of portability and versatility as disclosed by the present invention. The development of the odor absorbing and controlling device fulfills this need.

A search of the prior art did not disclose any patents that read directly on the claims of the instant invention; however, the following references were considered related:

U.S. Pat. No. 6,926,862 B2, issued in the name of Fontenot et al.;
U.S. Pat. No. 6,245,697 B1, issued in the name of Conrad et al.;
U.S. Pat. No. 3,101,488, issued in the name of Peebles;
U.S. Pat. No. 6,578,910 B2, issued in the name of Andersson et al.;
U.S. Pat. No. 7,559,610 B1, issued in the name of Hong Min;
U.S. Pat. No. 5,665,081, issued in the name of Grosse;
U.S. Pat. No. 6,313,371 B1, issued in the name of Conant et al.;
U.S. Pat. No. 4,928,681, issued in the name of Langston et al.;
U.S. Patent Application no. 2005/0015882 A1, published in the name of Huza;
U.S. Patent Application no. 2013/0045252, published in the name of Rawlings et al.; and
South Korean Patent Application no. KR 20120110772, published in the name of Seok.

This application presents claims and embodiments that fulfill a need or needs not yet satisfied by the products, inventions and methods previously or presently available. In particular, the claims and embodiments disclosed herein describe an odor absorbing and controlling device, the device comprising an odor control article and an adjustable holding component detachably secured thereto, wherein the article comprises a replaceable panel structure comprising a top panel structure and a bottom panel structure, the bottom panel structure being releasably attachable to the top panel structure; the top panel structure is enclosed via a fabric casing, the bottom panel structure is enclosed via a fabric casing, the top panel structure comprises a double woven textile material, the textile material includes a suitable and effective odor absorbing, neutralizing, controlling, removing and/or adsorbing material, the double woven textile material comprises an activated charcoal fibre cloth, and wherein the bottom panel structure comprises a polymer, resilient cushion material which may comprise a suitable and effective odor absorbing, neutralizing, controlling, removing and/or adsorbing material, the odor absorbing and controlling device providing unanticipated and nonobvious combination of features distinguished from the products, inventions and methods preexisting in the art. The applicant is unaware of any product, method, disclosure or reference that discloses the features of the claims and embodiments disclosed herein.

SUMMARY OF THE INVENTION

Briefly described according to one embodiment of the present invention, an odor absorbing and controlling device is disclosed. The device of the present invention comprises an odor control article and an adjustable holding component detachably secured thereto. The article comprises a replaceable panel structure comprising a top panel structure releasably attachable to a bottom panel structure via a fastening means. The top panel structure comprises a double woven textile material enclosed by a fabric casing.

In accordance to one embodiment, the top panel structure comprises an upper layer and a lower layer, the upper layer and lower layer jointly forming a structural body enclosed by a fabric casing.

The upper layer of top panel structure comprises a double woven textile material, and the lower layer comprises a foam or cellular polymer, resistant cushion material. The polymer foam construction material is incorporated with a suitable and effective odor absorbing, neutralizing, controlling, removing and/or adsorbing material, such as activated carbon or activated charcoal. The double woven textile material comprises activated charcoal fiber cloth.

The bottom panel structure comprises a foam or cellular polymer, resilient cushion material. The bottom panel structure is enclosed via a fabric casing. The foam cushion material of bottom panel structure is incorporated with a suitable and effective odor absorbing, neutralizing, controlling, removing and/or adsorbing material, such as activated carbon or activated charcoal.

The adjustable holding component is detachably secured to the odor control article, or replaceable panel structure, via an attachment mechanism. The holding component is adjustable from an elongated shoulder strap to a shortened handle.

In accordance to another embodiment, the odor absorbing and controlling device is sizably adapted and configured to be integrated with or utilized in conjunction with bedding, or otherwise supplant conventional bedding to absorb, control, remove and/or neutralize malodors associated with flatulence while resting and sleeping on a conventional bed, or other home furnishing articles, such as a sofa or couch.

In further accordance to this alternate embodiment, the odor absorbing and controlling bedding includes a blanket comprising a woven textile material enveloped by a fabric casing. The woven textile material comprises an activated charcoal, fibre cloth, or activated carbon fibre cloth.

In accordance to another alternate embodiment, a mattress support is disclosed, wherein the mattress support comprises an upper layer and a lower layer, the upper layer and lower layer jointly forming a structural body. The upper layer comprises a foam or cellular polymer, resilient cushion material, and the lower layer comprises a double woven textile material. The polymer, resilient cushion material of upper layer is incorporated with a suitable and effective odor absorbing, neutralizing, controlling, removing and/or adsorbing material, wherein the suitable and effective odor absorbing, neutralizing, controlling, removing and/or adsorbing material is preferably an activated carbon or activated charcoal. The double woven textile material of lower layer is disposed with an odor absorbing and controlling and/or removal material, such as an activated charcoal fibre cloth, or activated carbon fibre cloth.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 11 is a top plan, partially sectional view of a bottom panel structure of an odor absorbing and controlling device, according to one embodiment of the present invention;

FIG. 12 is a bottom plan view of the bottom panel structure of FIG. 11, according to one embodiment of the present invention;

FIG. 13 is a side elevational, cross-sectional view, on an enlarged scale, of the bottom panel structure of FIG. 13, in accordance to one embodiment of the present invention;

FIG. 14 is an exploded side elevational, partially sectional view illustrating releasable attachment of the top panel structure to the bottom panel structure of the device of FIG. 6, in accordance to one embodiment of the present invention;

FIG. 18 is a perspective view of an odor absorbing and controlling sleeping bed device, in accordance to another embodiment of the present invention;

DESCRIPTION OF THE PREFERRED EMBODIMENT

Detailed Description of the Figures

Figure 1:
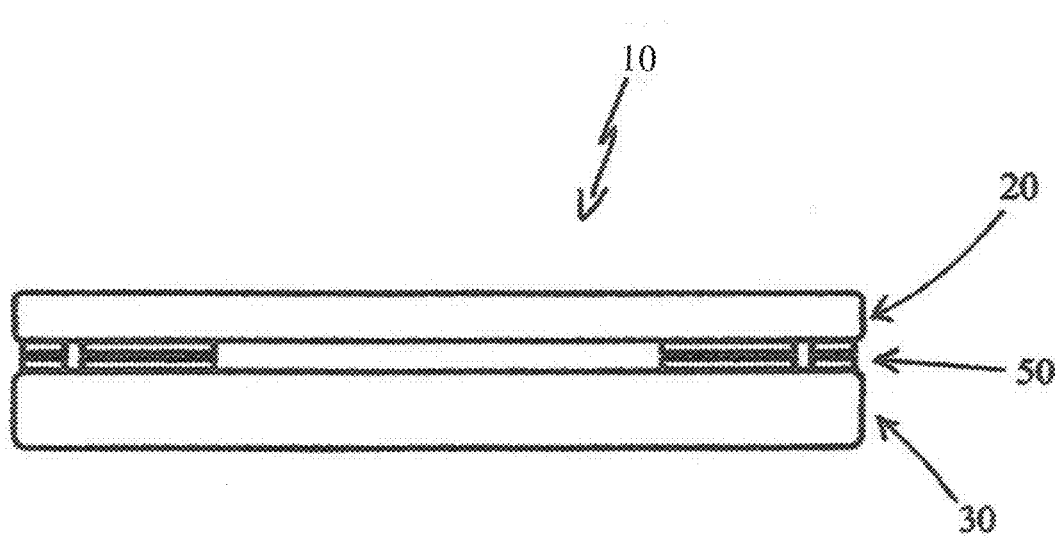
FIG. 1 is a side elevational view of an odor absorbing and controlling device, according to one embodiment of the present invention.
Figure 2:
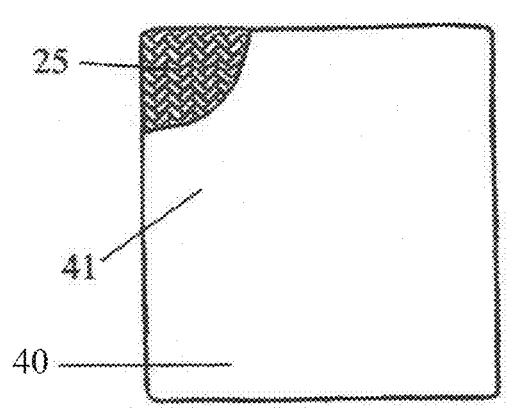
FIG. 2 is a top plan, partially sectional view of a top panel structure of the odor absorbing and controlling device, according to one embodiment of the present invention.
Figure 3:
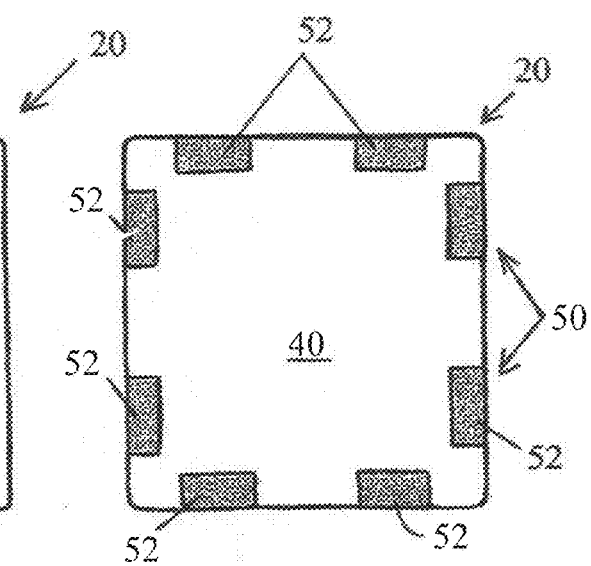
FIG. 3 is a bottom plan view of a top panel structure of the odor absorbing and controlling device, according to one embodiment of the present invention.
Figure 5:
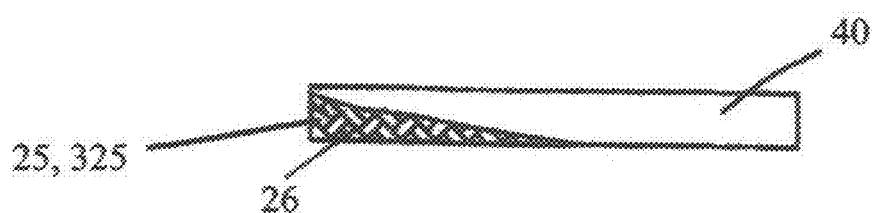
FIG. 5 is a side elevational, partially sectional view, on an enlarged scale, of the top panel structure of FIG. 2, in accordance to one embodiment of the present invention.
Figure 4:
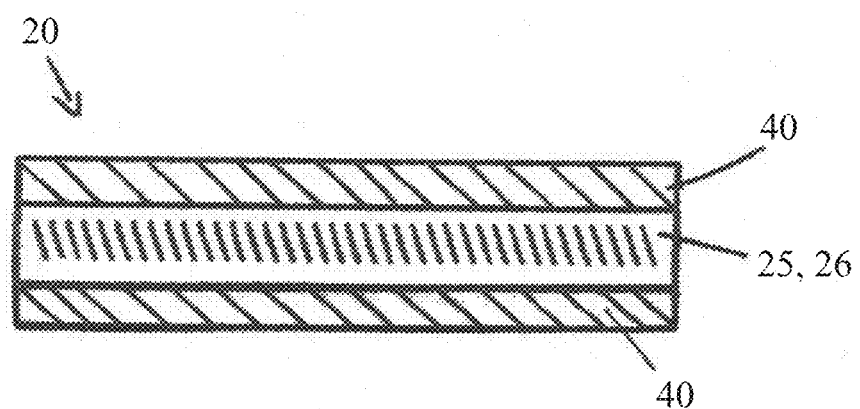
FIG. 4 is a cross-sectional view, on an enlarged scale, of the top panel structure of FIG. 2, in accordance to one embodiment of the present invention.
Figure 6:
FIG. 6 is a side elevational view of an odor absorbing and controlling device, in accordance to one embodiment of the present invention.
Figure 5A:
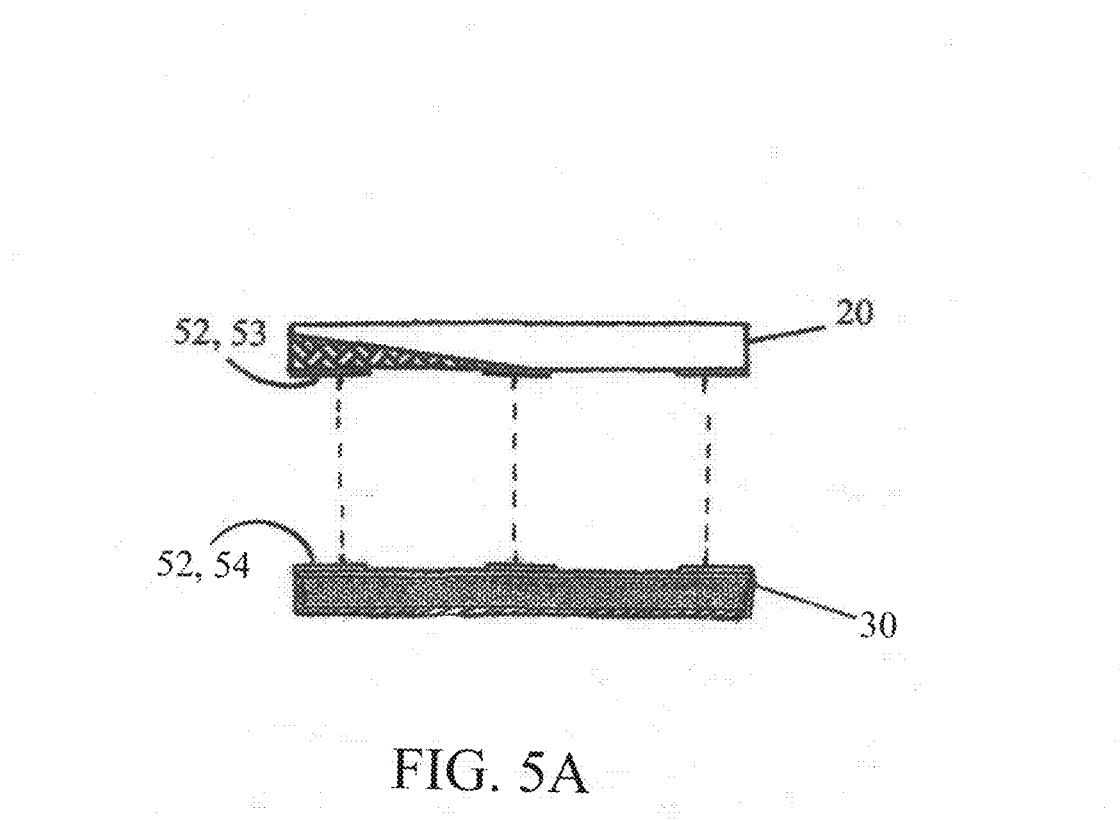
FIG. 5A is an exploded side elevational, partially sectional view illustrating releasable attachment of the top panel structure to the bottom panel structure, in accordance to one embodiment of the present invention.

Referring now to FIGS. 1-5A, an odor absorbing and controlling device 10 is disclosed, according to one embodiment of the present invention, the odor absorbing and controlling device 10, hereinafter "device 10", comprises a top panel structure 20 and a bottom panel structure 30, the bottom panel structure 30 being releasably attachable to the top panel structure 20 via a fastening means 50. The top panel structure 20 comprises a woven textile material 25 enveloped by a fabric casing 40 sewn together along perimeter sides thereof so as to enclose the woven textile material 25. The woven textile material 25 may be further defined as a double woven fabric.

The fabric casing 40 is constructed from natural and/or synthetic materials and sources. The fabric casing 40 may be constructed of a textile material selected from the group which includes, but is not limited to, cotton, cotton-polyester blend, linen, or other suitable natural and/or synthetic textile material, and/or combination thereof. In accordance to one embodiment, the fabric casing 40 may include a plurality of spatially-oriented pore openings, or small or micro apertures 41. The fabric casing 40, or top panel cover, comprises an unlimited design, shape, and/or color.

The woven textile material 25 disposed with an odor absorbing, neutralizing, controlling, removing and/or adsorbing material 325. In accordance to one embodiment, the woven textile material 25 comprises an odor absorbing, neutralizing, controlling, removing and/or adsorbing material 325 comprising activated charcoal fibers (or "fibres"), thereby forming a double woven activated charcoal fiber (or fibre) cloth 26. According to one embodiment, the activated charcoal fiber cloth 26 is constructed of polyacrylonitrile fibers. The polyacrylonitrile fibers (or "fibres") are manufactured using a process which includes heat-treating the polyacrylonitrile fibers in the process of carbonization and activation. More specifically, carbon fibres are created when polyacrylonitrile fibres, pitch resins (e.g., petroleum pitch, coal-tar pitch), or rayon are carbonized (through oxidation and thermal pyrolysis) at high temperatures. In addition, through further processes of graphitizing or stretching, the fibres strength or elasticity can be enhanced respectively. The carbon fibres may be manufactured in diameters ranging from approximately 6.0 micrometers ($\mu$m) to 20 micrometers ($\mu$m). The carbon fibres may be wound into larger threads for transportation and further production processes, which may include weaving or braiding into carbon fabrics and cloths.

In accordance to another embodiment, the textile material 25 may be impregnated into the cloth 26, coated with granular activated carbon, and/or otherwise dispersed with granular activated carbon using conventional techniques and processes for facilitating activated carbon dispersion about the cloth, such as a cloth incorporating granular activated carbon-filled permeable chambers.

Referring now to FIGS. 6-10, in accordance to one embodiment, the top panel structure 20a comprises an upper layer 22 and a lower layer 24, the upper layer 22 and lower layer 24 jointly forming a structural body 28. A fabric casing 40a sewn together along perimeter sides encloses the structural body 28, and wherein the fabric casing 40a may include a plurality of spatially-oriented pore openings, or small or micro apertures 41a. The fabric casing 40a, or top panel cover, comprises an unlimited design and/or color.

The upper layer 22 of top panel structure 20a comprises a woven textile material 25a, and the lower layer 24 comprises a foam or cellular polymer, resistant cushion material 123. The woven textile material 25a may be further defined as a double woven fabric. The woven textile material 25a is disposed with an odor absorbing, neutralizing, controlling, removing and/or adsorbing material 25aa. In accordance to one embodiment, the woven textile material 25a comprises an odor absorbing, neutralizing, controlling, removing and/or adsorbing material 25aa comprising activated charcoal fibers (or "fibres"), thereby forming a double woven activated charcoal fiber (or fibre) cloth 26a. For purposes of brevity and obviating redundancy, the woven textile material 25a and double woven activated charcoal fiber cloth 26a is constructed of the same materials, and implements the same construction methods and systems, including features, and advantages associated with, and in accordance to the embodiments as previously described hereinabove concerning the woven textile material 25 and double woven activated charcoal fiber cloth 26.

Figure 7:
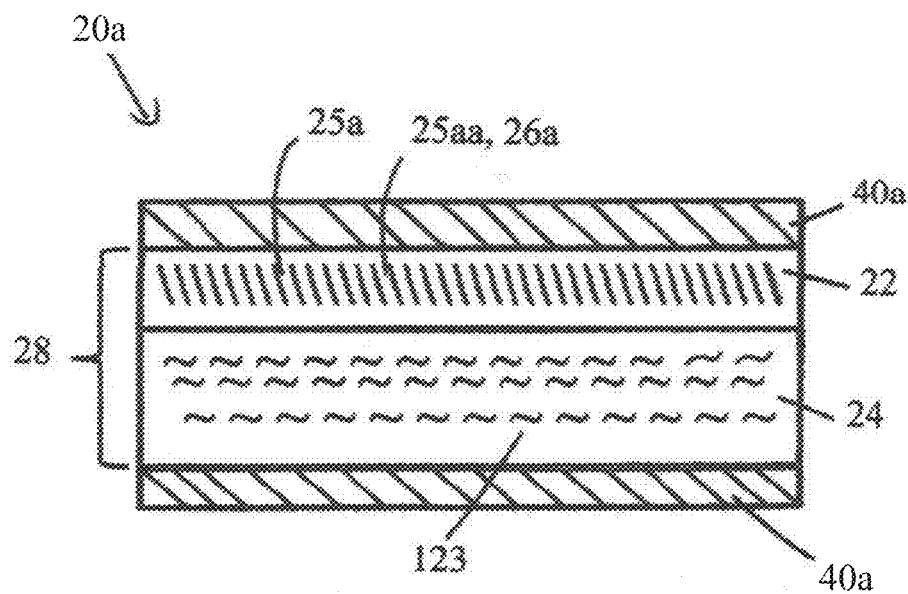
FIG. 7 is a cross-sectional view, on an enlarged scale, of the odor absorbing and controlling device of FIG. 6, in accordance to one embodiment of the present invention.
Figure 8:
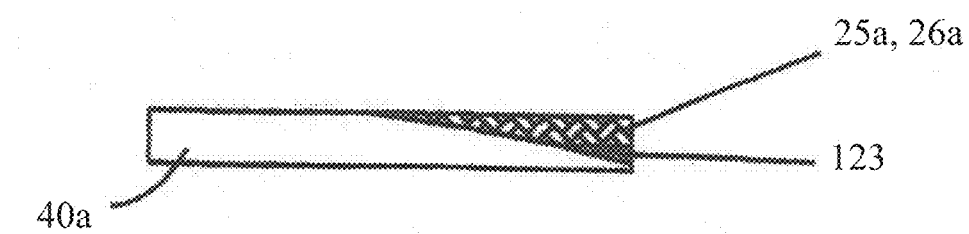
FIG. 8 is a side elevational, partially sectional view, on an enlarged scale, of the top panel structure portion of FIG. 6, in accordance to one embodiment of the present invention.
Figure 9:
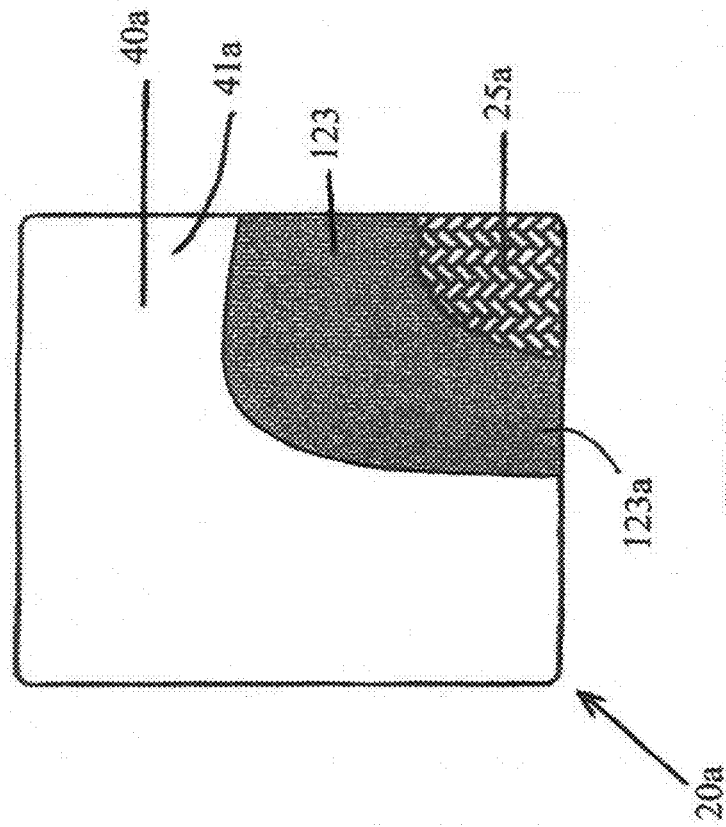
FIG. 9 is a top plan, partially sectional view of the top panel structure of FIG. 6, according to one embodiment of the present invention.
Figure 10:
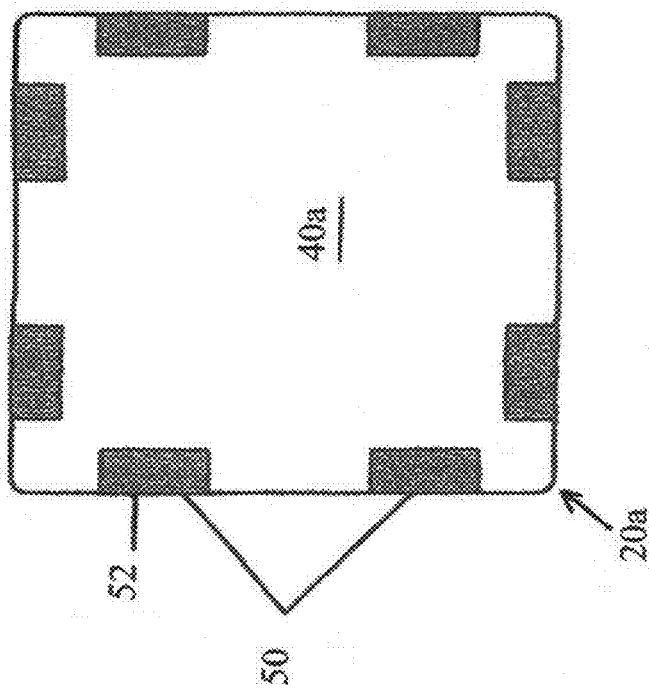
FIG. 10 is a bottom plan view of the top panel structure of FIG. 9, according to one embodiment of the present invention.

In reference to FIGS. 7-9, in accordance to one embodiment, the cushion material 123 of lower layer 24 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 123 is integrated with a suitable and effective odor absorbing, neutralizing, controlling, removing and/or adsorbing material 123a via a suitable dispersion method. The suitable and effective odor absorbing, neutralizing, controlling, removing and/or adsorbing material 123a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 123 meets respective state flammability requirements.

Figure 15:
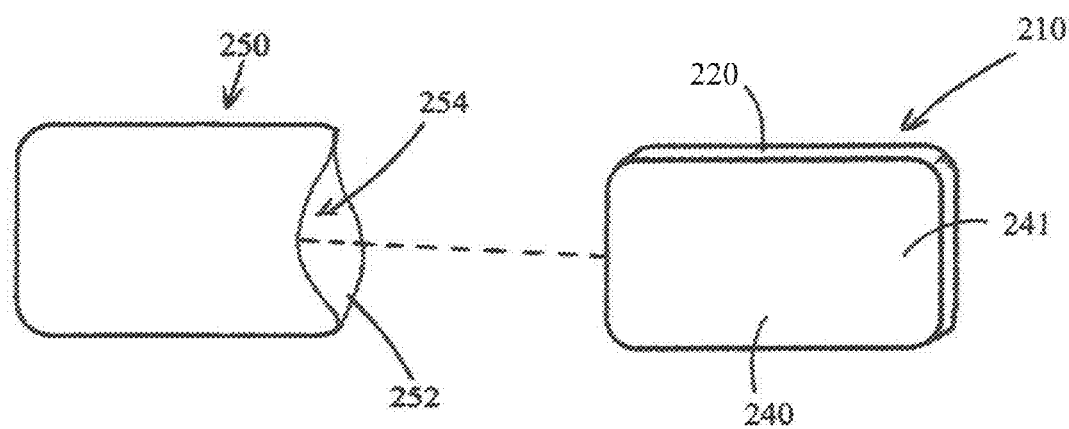
FIG. 15 is an exploded perspective view of a panel structure of illustrating the insertion thereof into a fabric casing.
Figure 15B:
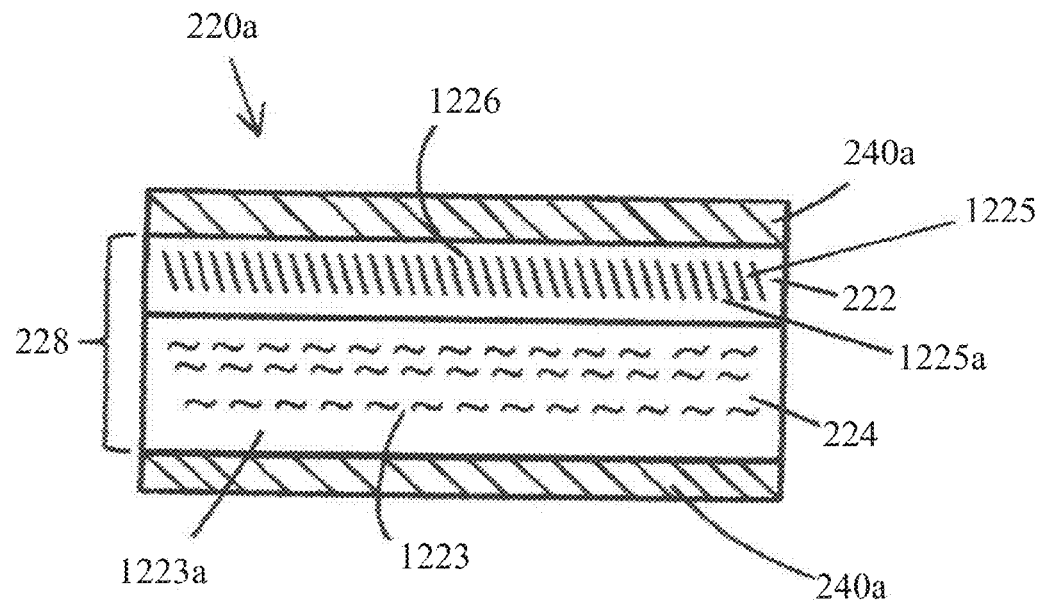
FIG. 15B is a cross-sectional view, on an enlarged scale, of a panel structure, in accordance to an alternate embodiment of the present invention.

Referring now to FIGS. 15-15B, an odor absorbing and controlling device 210 adapted as a removable insert within a flexible casing 250 is disclosed, in accordance to an alternate embodiment of the present invention.

Figure 15A:
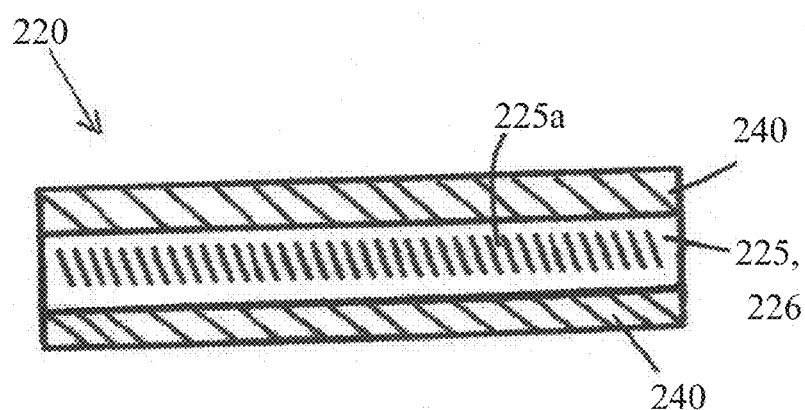
FIG. 15A is a cross-sectional view, on an enlarged scale, of the panel structure of FIG. 15, in accordance to one embodiment of the present invention.

Referring now more specifically to FIGS. 15-15A, in accordance to one embodiment, the odor absorbing and controlling device 210 comprises a replaceable panel structure 220. The panel structure 220 comprises a woven textile material 225 enveloped by a fabric casing 240 sewn together along perimeter sides thereof so as to enclose the woven textile material 225.

The fabric casing 240 is constructed from natural and/or synthetic materials and sources. The fabric casing 240 may be constructed of a textile material selected from the group which includes, but is not limited to, cotton, cotton-polyester blend, linen, or other suitable natural and/or synthetic textile material, and/or combination thereof. In accordance to one embodiment, the fabric casing 240 may include a plurality of spatially-oriented pore openings, or small or micro apertures 241. The fabric casing 240, or top panel cover, comprises an unlimited design, shape, and/or color.

The woven textile material 225 may be further defined as a double woven fabric. The woven textile material 225 is disposed with an odor absorbing, neutralizing, controlling, removing and/or adsorbing material 225a. In accordance to one embodiment, the woven textile material 225 comprises an odor absorbing, neutralizing, controlling, removing and/or adsorbing material 225a comprising activated charcoal fibers (or "fibres"), thereby forming a double woven activated charcoal fiber (or fibre) cloth 226. For purposes of brevity and obviating redundancy, the woven textile material 225 and double woven activated charcoal fiber cloth 226 is constructed of the same materials, and implements the same construction methods and systems, including features, and advantages associated with, and in accordance to the embodiments as previously described hereinabove concerning the woven textile material 25, 25a and double woven activated charcoal fiber cloth 26, 26a.

Referring now to FIG. 15B, in accordance to another embodiment, the odor absorbing and controlling device 210 comprises a replaceable panel structure 220a comprising an upper layer 222 and a lower layer 224, the upper layer 222 and lower layer 224 suitably affixed to one another and jointly forming a structural body 228.

The upper layer 222 of panel structure 220a comprises a woven textile material 1225, and the lower layer 224 comprises a foam or cellular polymer, resistant cushion material 1223. The woven textile material 1225 may be further defined as a double woven fabric.

The woven textile material 1225 is disposed with an odor absorbing, neutralizing, controlling, removing and/or adsorbing material 1225a. In accordance to one embodiment, the woven textile material 1225 comprises an odor absorbing, neutralizing, controlling, removing and/or adsorbing material 1225a comprising activated charcoal fibers (or "fibres"), thereby forming a double woven activated charcoal fiber (or fibre) cloth 1226.

In accordance to one embodiment, the cushion material 1223 of lower layer 224 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 1223 is integrated with a suitable and effective odor absorbing, neutralizing, controlling, removing and/or adsorbing material 1223a via a suitable dispersion method. The suitable and effective odor absorbing, neutralizing, controlling, removing and/or adsorbing material 1223a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 1223 meets respective state flammability requirements.

A fabric cover 240a sewn together along perimeter sides thereof encloses the structural body 228, and wherein the fabric cover 240a may include a plurality of spatially-oriented pore openings, or small or micro apertures. The fabric cover 240a may be constructed of a textile material selected from the group which includes, but is not limited to, cotton, cotton-polyester blend, linen, or other suitable natural and/or synthetic textile material, and/or combination thereof.

A flexible fabric casing 250 is disclosed for slidably receiving and housing the odor absorbing and controlling device 210 in a size-accommodative, snug-fit manner. The flexible fabric casing 250 may be constructed of a cotton fabric material or other suitably desired material. The casing 250 is preferably constructed of a material characterized as washable, thereby providing a reusable casing 250. The flexible fabric casing 250 comprises a pair of panels sewn about respective top, bottom, and rear side edges thereof, forming an interior cavity 254. The forward side edges of the respective panels of casing 250 are unattached so as to define an insert opening 252 providing open, direct passage into the interior cavity 254 of casing 250.

In accordance to one embodiment, the forward side edges of respective panels of the casing 250 may be disposed with a fastening means (not shown) for closing the forward side of panels in a releasably secured manner, thereby providing a closable opening. Fastening means may include a hook-and-loop fastening system (Velcro®) or other suitable fastening devices or complementary type or matching connector devices and systems which include, but are not limited to, snap-fit mechanisms, mechanical interference or frictional fit connection systems, zippers, magnetic devices, adhesive strips with releasable liners, or other similar devices, and combinations thereof.

Figure 15C:
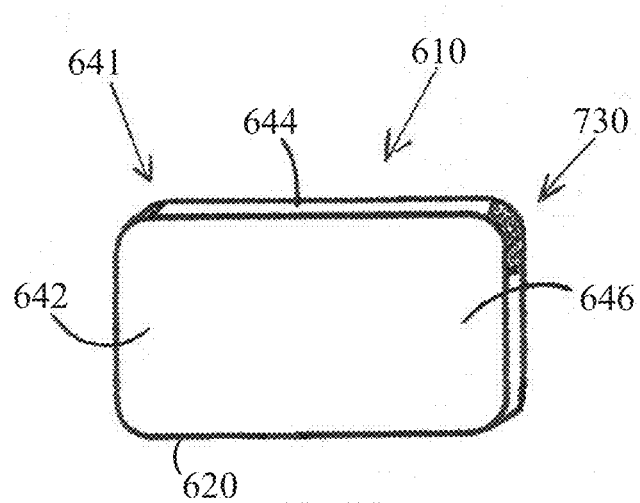
FIG. 15C is a front, top-let left perspective view of a replaceable panel structure, in accordance to one embodiment of the present invention.
Figure 15D:
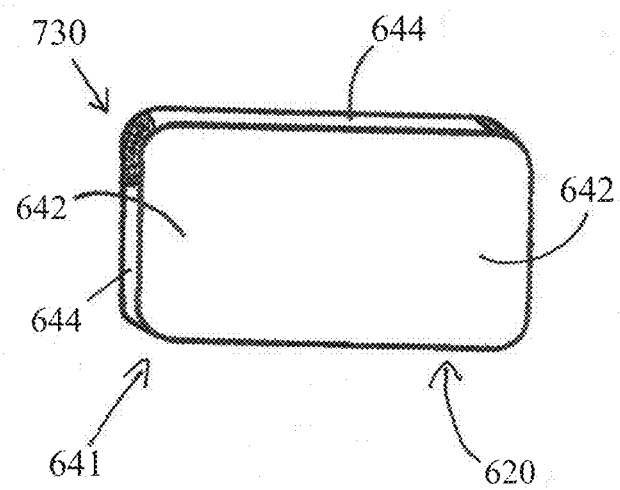
FIG. 15D is a front, top right perspective view of the panel structure of FIG. 15C.
Figure 15F:
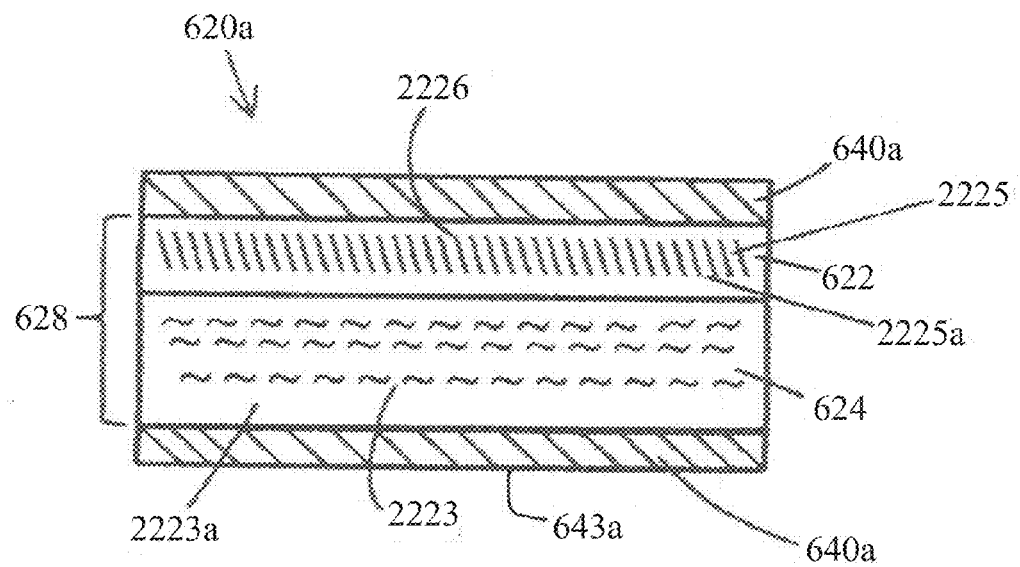
FIG. 15F is a cross-sectional view, on an enlarged scale, of a panel structure, in accordance to another embodiment of the present invention.
Figure 15E:
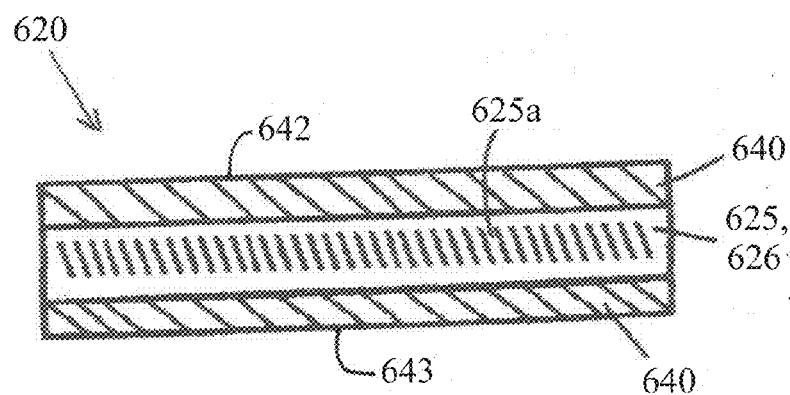
FIG. 15E is a cross-sectional view, on an enlarged scale, of the panel structure of FIGS. 15B and 15C, in accordance to one embodiment of the present invention.
Figure 15G:
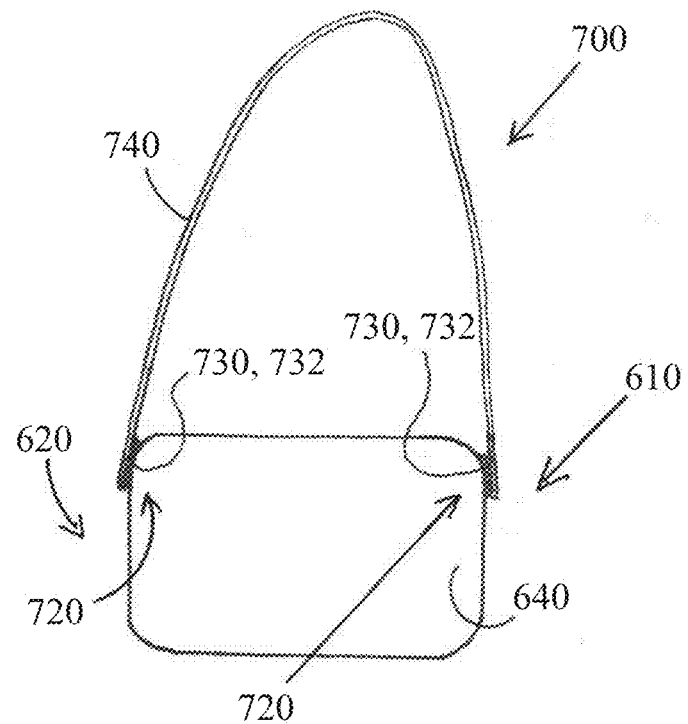
FIG. 15G is a front perspective view of an odor control device illustrating an adjustable holding component in the form of a shoulder strap detachably secured thereto, in accordance to one embodiment of the present invention.

Referring now more particularly to FIGS. 15C, 15D, and 15G, an odor control device 610 is disclosed, wherein the device 610 comprises a replaceable panel structure 620 to which an adjustable holding component 700 is detachably secured. The panel structure 620 further comprises a woven textile material 625 enveloped by a fabric casing 640 forming an odor control article 641. The fabric casing 640 is sewn together along perimeter sides of the woven textile material 625, enclosing the woven textile material 625. The odor control article 641 comprises a top 642 opposing a bottom 643, and a continuous, upwardly-extending sidewall 644 integrally joining the top 642 and bottom 643.

The fabric casing 640 is constructed from natural and/or synthetic materials and sources. The fabric casing 640 may be constructed of a textile material selected from the group which includes, but is not limited to, cotton, cotton-polyester blend, linen, or other suitable natural and/or synthetic textile material, and/or combination thereof. In accordance to one embodiment, the fabric casing 640 may include a plurality of spatially-oriented pore openings, or small or micro apertures 646. The fabric casing 640, or panel cover, comprises an unlimited design, shape, and/or color.

The woven textile material 625 may be further defined as a double woven fabric. The woven textile material 625 is disposed with an odor absorbing, neutralizing, controlling, removing and/or adsorbing material 625a. In accordance to one embodiment, the woven textile material 625 comprises an odor absorbing, neutralizing, controlling, removing and/or adsorbing material 625a comprising activated charcoal fibers (or "fibres"), thereby forming a double woven activated charcoal fiber (or fibre) cloth 626. For purposes of brevity and obviating redundancy, the woven textile material 625 and double woven activated charcoal fiber cloth 626 is constructed of the same materials, and implements the same construction methods and systems, including features, and advantages associated with, and in accordance to the embodiments as previously described hereinabove concerning the woven textile material 25, 25a and double woven activated charcoal fiber cloth 26, 26a.

Referring now to FIG. 15F, and FIGS. 15L-15N, in accordance to another embodiment, the odor absorbing and controlling device 610 comprises a replaceable panel structure 620a comprising an upper layer 622 and a lower layer 624, the upper layer 622 and lower layer 624 suitably affixed to one another and jointly forming a structural body 628.

The upper layer 622 of panel structure 620a comprises a woven textile material 2225, and the lower layer 624 comprises a foam or cellular polymer, resistant cushion material 2223. The woven textile material 2225 may be further defined as a double woven fabric.

The woven textile material 2225 is disposed with an odor absorbing, neutralizing, controlling, removing and/or adsorbing material 2225a. In accordance to one embodiment, the woven textile material 2225 comprises an odor absorbing, neutralizing, controlling, removing and/or adsorbing material 2225a comprising activated charcoal fibers (or "fibres"), thereby forming a double woven activated charcoal fiber (or fibre) cloth 2226.

In accordance to one embodiment, the cushion material 2223 of lower layer 624 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 2223 is integrated with a suitable and effective odor absorbing, neutralizing, controlling, removing and/or adsorbing material 2223a via a suitable dispersion method. The suitable and effective odor absorbing, neutralizing, controlling, removing and/or adsorbing material 2223a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 2223 meets respective state flammability requirements.

A fabric cover 640a sewn together along perimeter sides thereof encloses the structural body 628, forming an odor control article 641a. The fabric cover 640a is sewn together along perimeter sides of the structural body 628, enclosing the body 628. The odor control article 641a comprises a top 642 opposing a bottom 643, and a continuous, upwardly-extending sidewall 644 integrally joining the top 642 and bottom 643. The fabric cover 640a may include a plurality of spatially-oriented pore openings, or small or micro apertures. The fabric cover 640a may be constructed of a textile material selected from the group which includes, but is not limited to, cotton, cotton-polyester blend, linen, or other suitable natural and/or synthetic textile material, and/or combination thereof.

Figure 15H:
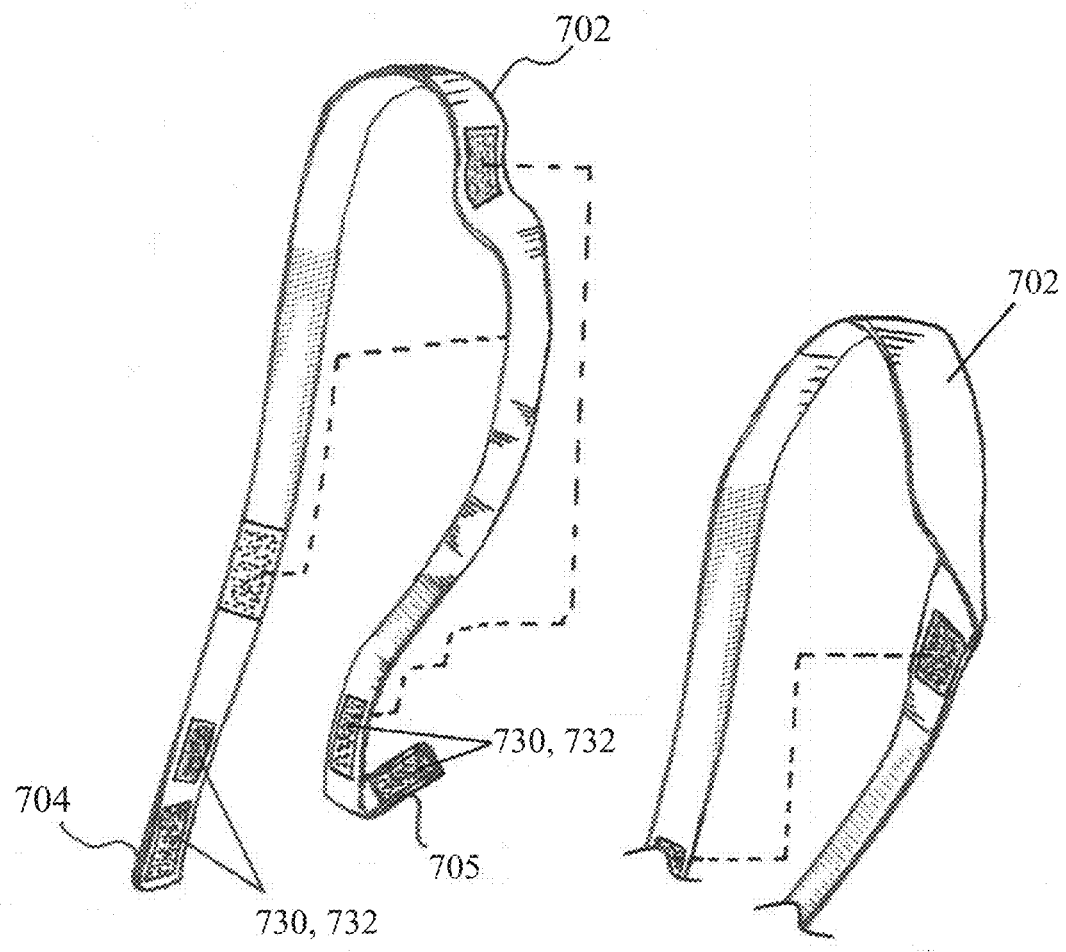
FIG. 15H is an exploded perspective view of an adjustable elongated strap disposed with complementary couplers, in accordance to one embodiment of the present invention.
Figure 15I:
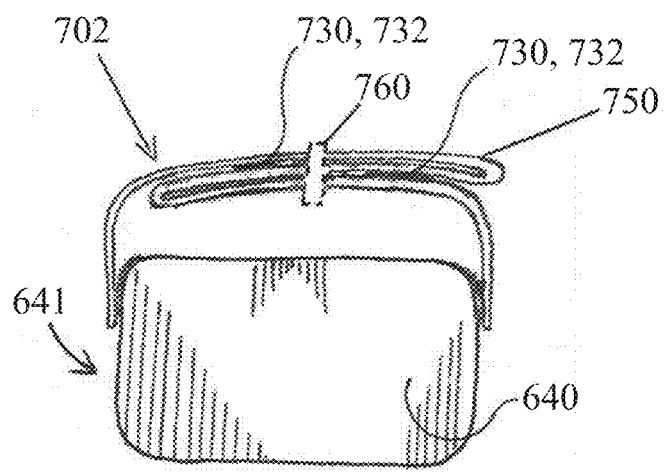
FIG. 15I is a front perspective view of an odor control device illustrating the holding component adjusted to form a shortened handle, in accordance to one embodiment of the present invention.
Figure 15J:
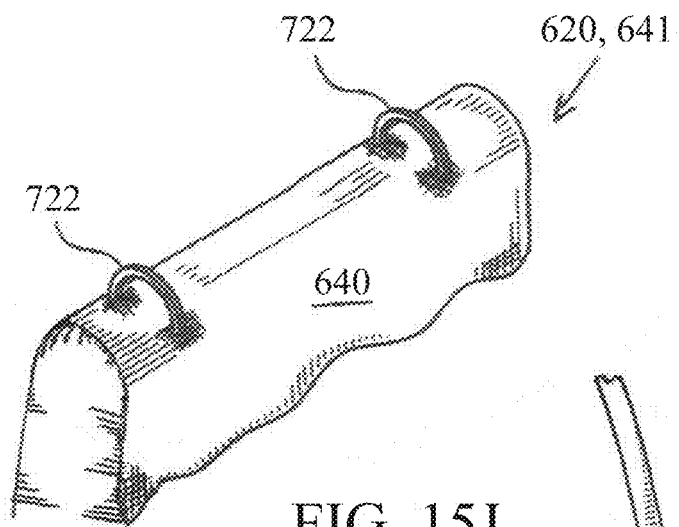
FIG. 15J is a partial perspective view of an odor control device, in accordance to one embodiment of the present invention.
Figure 15K:
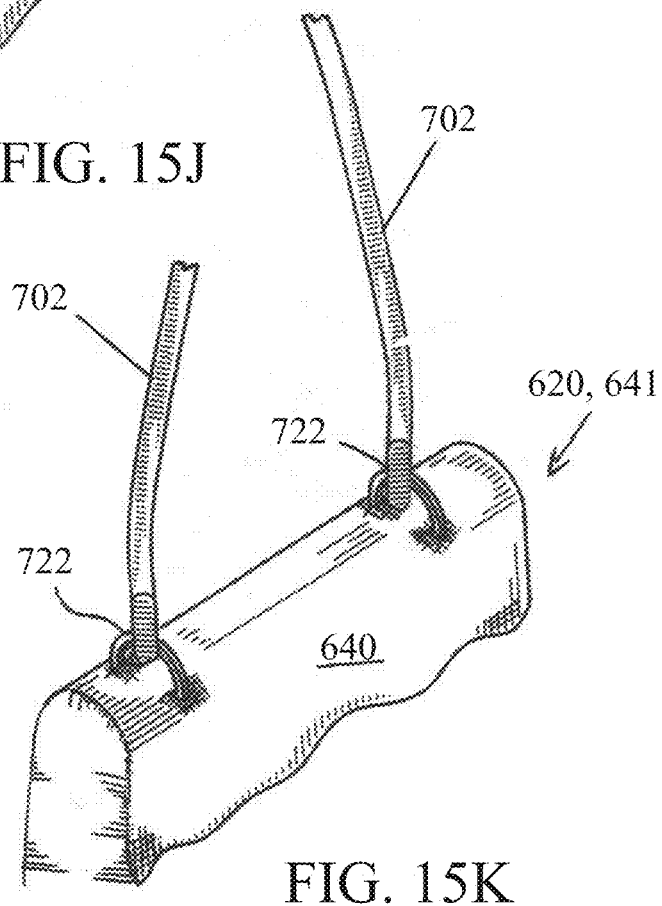
FIG. 15K is a partial perspective view of the odor control device of FIG. 15J illustrating an adjustable holding component detachably secured thereto, in accordance to one embodiment of the present invention.
Figure 15L:
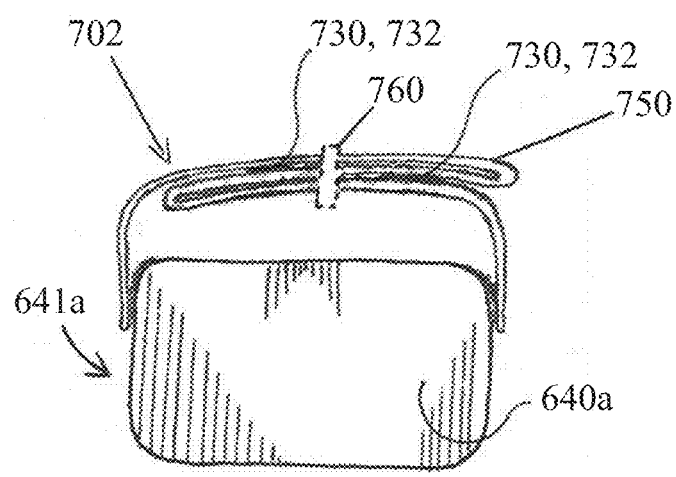
FIG. 15L is a front perspective view of an odor control device illustrating the holding component adjusted to form a shortened handle, in accordance to another embodiment of the present invention.
Figure 15M:
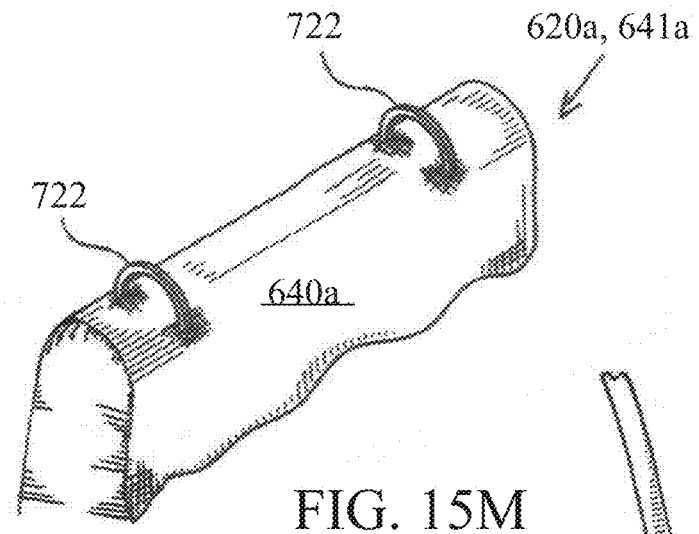
FIG. 15M is a partial perspective view of an odor control device, in accordance to another embodiment of the present invention.

In reference to FIGS. 15G, 15H, and 15L, the adjustable holding component 700 is detachably secured to the odor control article 641, 641a or panel structure 620, 620a via an attachment mechanism 720. The holding component 700 comprises an adjustable elongated strap 702 or tether, constructed of a lightweight, flexible material, and includes a first free end 704 and a second free end 705. Suitable construction materials for constructing the strap 702 include, but are not limited to, nylon, high quality polyester, polypropylene, cotton, leather, and/or a combination thereof. The strap 702 comprises a length suitable for supporting the odor control article 641, 641a in a suspended manner from a user's shoulder or shoulders, thereby providing a shoulder strap 740. When the strap 702 is attached to the odor control article 641, 641a such that the strap 702 is oriented in an extended or elongated condition (shoulder strap 740 condition) in the manner as previously described, the article 641, 641a may be transported hands-free by the user.

The attachment mechanism 720 comprises complementary couplers 730 affixed to the first and second free ends 704 and 705 of strap 702 and to at least two sections of the continuous sidewall 644 of the odor control article 641, 641a. In accordance to one embodiment, the complementary couplers 730 are illustrated in FIGS. 15G-15I as hook-and-loop fasteners 732, namely, the Velcro® brand hook-and-loop fastener. The first free end 704 and second free end 705 each includes a hook portion of the hook-and-loop fastener 732 suitably attached thereto, such as via sewing. Loop portions of the hook-and-loop fastener 732 are suitably attached, such as via sewing, distally to sections of the continuous sidewall 644, as shown in FIGS. 15C and 15D. The hook portions of the first and second free ends 704 and 705 engage the loop portions of the continuous sidewall 644 of odor control article 641, 641a, respectively, thereby detachably securing the strap 702 to the article 641, 641a or panel structure 620. It is envisioned and therefore within the scope of the present invention that the hook and loop portions of the hook-and-loop fasteners 732 may be arranged in vice-versa fashion; e.g., the loop portions of the hook-and-loop fastener 732 may be suitably attached, respectively, to each the first free end 704 and second free end 705 of strap 702, and the hook portions of the hook-and-loop fastener 732 may be suitably attached distally to sections of the continuous sidewall 644. Significantly, both the odor control article 641, 641a and attached holding component 700 are constructed entirely of nonmetallic materials, thereby preventing activation of metal detection security systems and devices, particularly such as metal detection systems employed in airports.

The elongated strap 702 is adjustable in length. The length of the elongated strap 702 may be decreased to a desired shorter length, fixed at the desired shorter length, and detachably secured to article 641, 641a via complementary couplers 730, thereby providing a handle 750 by which the odor control article 641, 641a may be supported (FIGS. 15I and 15L). The complementary couplers 730 are shown in FIGS. 15G-15I and FIG. 15L as being hook-and-loop fasteners 732; however, the couplers 730 may comprise other complementary type or matching connector devices and systems which include, but are not limited to, snap-fit mechanisms, mechanical interference or frictional fit connection systems, magnetic devices, adhesive strips with releasable liners, or other similar devices, and combinations thereof, or a plurality of each, or a plurality of each in combination with one or more alternatives.

In FIGS. 15I and 15L, the handle 750 is shown detachably secured to the odor control article 641, 641a. In reference to FIGS. 15H, 15I, and 15L, in order to detachably secure the strap 702 to a desired shortened length so as to form a handle 750, the strap 702 is provided with a plurality of complementary couplers 730 (illustrated as hook-and-loop fasteners 732) suitably attached spatially to various sections along the upper surface and lower surface of strap 702. To convert the holding component 700 from an elongated shoulder strap 740 into a shortened handle 750, the complementary couplers 730 are engaged with one another in a mutually-cooperative, overlapping fashion, and in the manner as delineated in the exploded view of FIG. 15H. The complementary couplers 730 may be attached spatially to other various sections along the upper surface and lower surface of strap 702 not illustrated herein, and thereafter engaged in a mutually-cooperative, overlapping fashion to decrease the length of the shoulder strap 740 so as to form a shortened handle 750.

It is contemplated that an auxiliary strap 760 (FIGS. 15I and 15L) may be included for detachably securing the overlapped strap sections of handle 750 in configuration being more tightly compressed and bound. The auxiliary strap 760 may be integrally connected to the holding component 700 or detachably secured in a winding-overlapping fashion therearound; for example, similar to the operation of winding fishing line around a conventional fishing reel. The auxiliary strap 760 is envisioned to include at least one complementary coupler, such as a hook-and-loop fastener 732, such that once the auxiliary strap 760 has been wound taut, in a transverse orientation, around the overlapped strap sections of the handle 750, the hook portion of the hook-and-loop fastener 732 is engaged in a mutually cooperative fashion with the loop portion thereof, thereby detachably securing the auxiliary strap 760 in the tautly wound position around the handle 750.

Figure 15N:
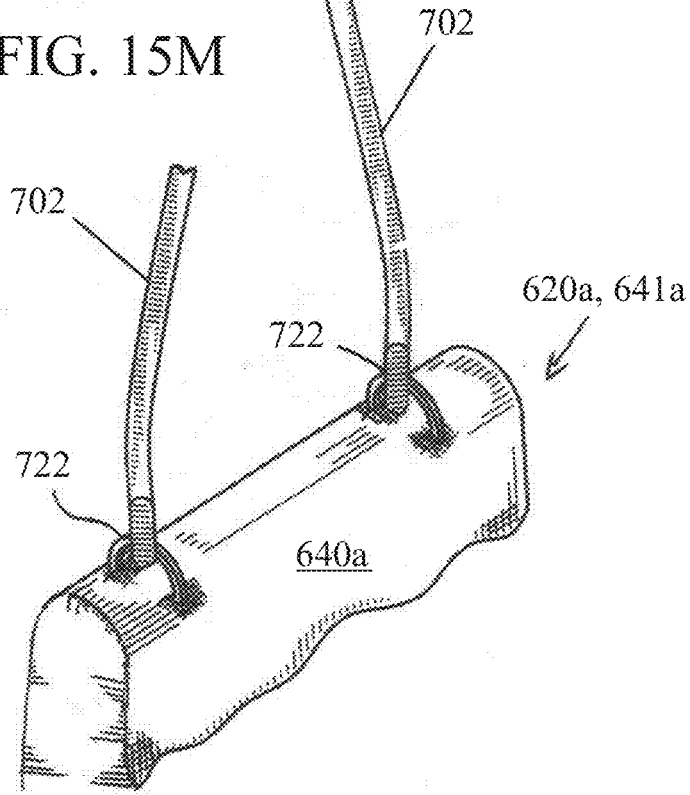
FIG. 15N is a partial perspective view of the odor control device of FIG. 15M illustrating an adjustable holding component detachably secured thereto, in accordance to one embodiment of the present invention.

Referring now more particularly to FIGS. 15J-15K and 15M-15N, in accordance to another embodiment, the attachment mechanism 720 may comprise a coupling arrangement, such as a pair of plastic D-rings 722, through which the free ends 704 and 705 of strap 702 are respectively looped and detachably secured via hook-and-loop fasteners 732 being suitably attached to each the first free end 704 and the second free end 705 of strap 702, as best illustrated in FIGS. 15K and 15N.

In accordance to one embodiment, the D-rings 722 are securely affixed to the odor control article 641, 641a by stitching the lower arm portions of each D-ring 722 to the lower surface and/or upper surface of the fabric casing 640, 640a. The D-rings 722 may also be securely affixed directly into the panel structure 620, 620a. The D-rings 722 may further be securely affixed to the odor control article 641, 641a or panel structure 620, 620a using other securing methods well known and readily apparent to those skilled in the art and are therefore within the spirit and scope of the present invention.

The D-rings 722 are preferably constructed of a lightweight, rigid plastic material so that when attached to the odor control article 641, 641a, metal detection security systems and devices, particularly such as metal detection systems employed in airports, are not activated by the article 610.

The D-rings 722 may also be constructed from other lightweight, rigid materials which may be selected from the group which includes, but is not limited to, wood, metal, or a metallic-plastic composite.

The attachment mechanism 720 may comprise other complementary type or matching connector devices and systems which include, but are not limited to, snap-fit mechanisms, mechanical interference or frictional fit connection systems, magnetic devices, adhesive strips with releasable liners, or other similar devices, and combinations thereof, or a plurality of each, or a plurality of each in combination with one or more alternatives.

Referring now to FIGS. 1, 5A, 6, and 11-14, the bottom panel structure 30 comprises a foam or cellular polymer, resilient cushion material 33. A fabric casing 60 sewn together along perimeter sides encloses the polymer, resistant cushion material 33, and wherein the fabric casing 60 may include a plurality of spatially-oriented pore openings, or small or micro apertures 61. The fabric casing 60 comprises an unlimited design, shape, and/or color, and wherein the unlimited design, shape, and/or color may be the same or match the design, shape, and/or color of the fabric casing 40, 40*a*, respectively, enclosing the top panel structure 20, 20*a*, and vice-versa.

In accordance to one embodiment, the cushion material 33 of bottom panel structure 30 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

The selected polymer foam construction material 33 is incorporated with (such as via a suitable dispersion method), a suitable and effective odor absorbing, neutralizing, controlling, removing and/or adsorbing material 34. The suitable and effective odor absorbing, neutralizing, controlling, removing and/or adsorbing material 34 is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 33 meets respective state flammability requirements.

Referring now more specifically to FIGS. 1, 3, 5A, 6, 10, 12, and 14, the bottom panel structure 30 is releasably attachable to the top panel structure 20, 20*a* via a suitable fastening means 50, such as a hook-and-loop fastening system 52, namely, the Velcro® brand hook-and-loop fastener. In accordance to one embodiment, the upper surface of the bottom panel structure 30 is releasably attached to the lower surface of the top panel structure 20. The lower surface of top panel structure 20 comprises a plurality of hook-and-loop fastener portions 53 spatially disposed about a perimeter thereof. The upper surface of the bottom panel structure 30 comprises a plurality of complementary hook-and-loop fastener portions 54 spatially disposed and aligned about a perimeter thereof for mutually-cooperative engagement with the plurality of hook-and-loop fastener portions 53 spatially disposed about the lower surface of top panel structure 20. The fastening means 50 may comprise other complementary type or matching connector devices and systems which include, but are not limited to, snap-fit mechanisms, mechanical interference or frictional fit connection systems, zipper, magnetic devices, adhesive strips with releasable liners, or other similar devices, and combinations thereof.

The top panel structure 20, 20*a* may be placed atop the seat portion of a chair (not shown), a bed, or other desired home furnishing articles, such as a sofa or couch to absorb, control, remove and/or neutralize malodors associated with flatulence while resting on a conventional bed, or other home furnishing articles, such as a sofa or couch (not shown). As the offensive odor of malodorous air passes through the fabric casing 40, 40*a* and into the structural body 28 of top panel structure 20, 20*a*, respectively, the malodorous air/gas is absorbed, removed, and/or neutralized by the activated carbon or activated charcoal, thereby preventing diffusion of malodorous air or gas beyond the top panel structure 20, 20*a* and thus controlling the offensive odor.

Further, the top panel structure 20, 20*a* may be used in combination with the bottom panel structure 30 (e.g., structure 20, 20*a* being releasably attached to structure 30) to provide a seat and/or back cushion which functions to absorb, control, remove and/or neutralize malodors associated with flatulence as previously described.

Figure 16:
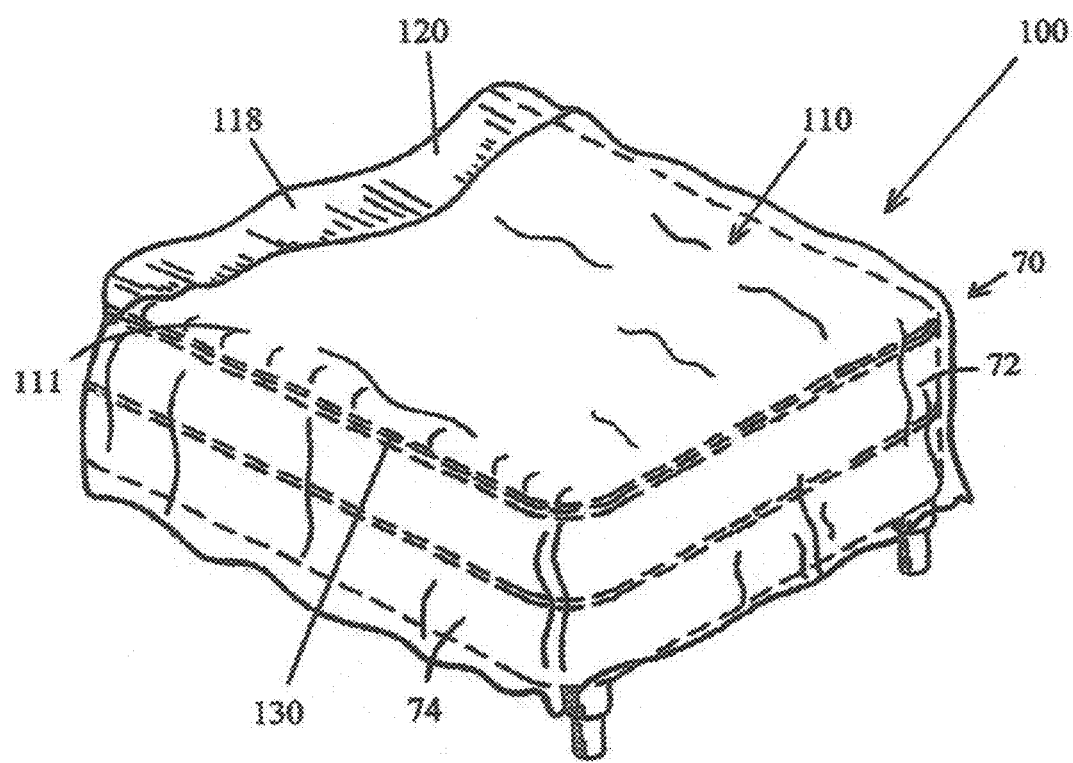
FIG. 16 is a perspective view of odor absorbing and controlling bedding, shown in-use with a conventional bed.
Figure 16A:
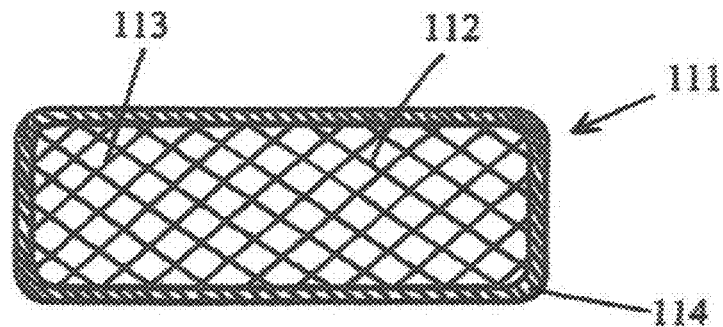
FIG. 16A is a cross-sectional view, on an enlarged scale, of a blanket of the odor absorbing and controlling bedding of FIG. 16, in accordance to one embodiment of the present invention.
Figure 17:
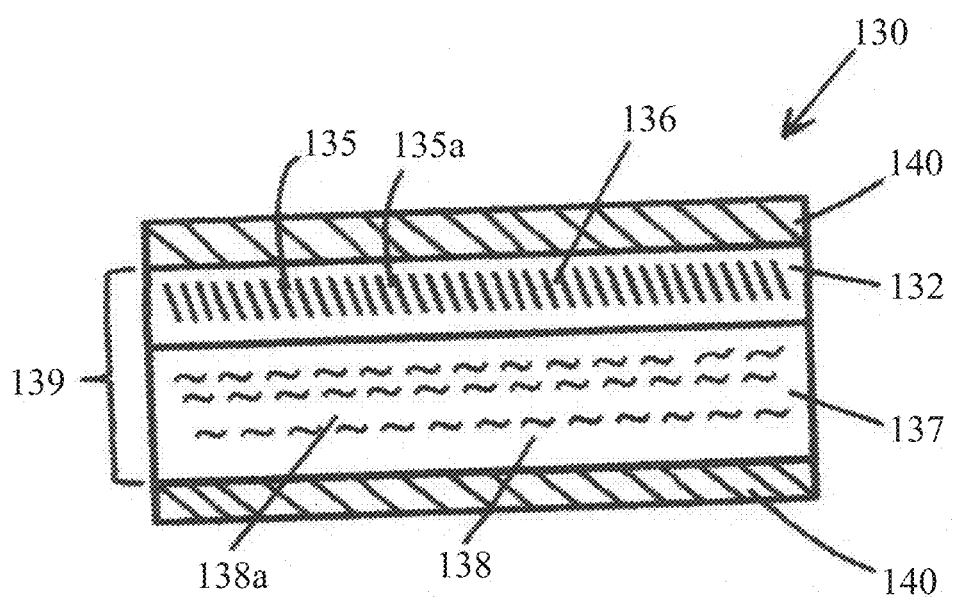
FIG. 17 is a cross-sectional view, on an enlarged scale, of a mattress support of the odor absorbing and controlling bedding of FIG. 16, in accordance to one embodiment of the present invention.

Referring now to FIGS. 16-17, and in accordance to another embodiment, the odor absorbing and controlling device 10 is sizably adapted and configured to be integrated with or utilized in conjunction with bedding, or otherwise supplant conventional bedding to absorb, control, remove and/or neutralize malodors associated with flatulence while resting and sleeping on a conventional bed 70, or other home furnishing articles, such as a sofa or couch (not shown). For purposes of this disclosure, a conventional bed 70 is defined as having an upper mattress 72 resting atop a lower box spring 74, and conventional bedding is defined herein as including a sheet and at least one blanket.

The odor absorbing and controlling bedding 100, in accordance to one embodiment, includes bedding 110 which includes a blanket 111 comprising a woven textile material 112 enveloped by a fabric casing 114, such as a cotton fabric casing. The fabric casing 114 may be sewn together along perimeter sides thereof so as to enclose the woven textile material 112. The woven textile material 112 comprises an activated charcoal, fibre cloth 113, or activated carbon fibre cloth.

The bedding 110 may further comprise a sheet 118 comprising a matrix 120 of fibers, the matrix 120 of fibers comprising a cotton, cotton-polyester blend, linen, or other suitable natural or synthetic textile material woven in or interwoven into activated charcoal or carbon fibres. The matrix 120 may be further described as a bonded web structure.

The sheet 118 may alternatively comprise a matrix which includes a nonwoven blend of fibres, wherein at least one of the fibres being activated charcoal or carbon fibres.

The odor absorbing and controlling bedding 100 is manufactured so as to be sized and dimensioned to accommodate single, twin, full, queen, king, California King, Eastern King beds, and the like.

In particular reference to FIGS. 16 and 17, a mattress support 130 is disclosed. The mattress support 130, in accordance to one embodiment, comprises an upper layer 132 and a lower layer 137, the upper layer 132 and lower layer 137 jointly forming a structural body 139.

The upper layer 132 comprises a woven textile material 135, and the lower layer 137 comprises a foam or cellular polymer, resistant cushion material 138. The woven textile material 135 may be further defined as a double woven fabric.

The woven textile material 135 is disposed with an odor absorbing, neutralizing, controlling, removing and/or adsorbing material 135*a*. In accordance to one embodiment, the woven textile material 135 comprises an odor absorbing, neutralizing, controlling, removing and/or adsorbing material 135*a* comprising activated charcoal fibers (or "fibres"), thereby forming a double woven activated charcoal fiber (or fibre) cloth 136. For purposes of brevity and obviating redundancy, the woven textile material 135 and double woven activated charcoal fiber cloth 136 is constructed of the same materials, and implements the same construction methods and systems, including features, and advantages associated with, and in accordance to the embodiments as previously described hereinabove concerning the woven textile material 25, 25a, 225 and double woven activated charcoal fiber cloth 26, 26a, 226.

In accordance to one embodiment, the cushion material 138 of lower layer 137 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 138 is integrated with a suitable and effective odor absorbing, neutralizing, controlling, removing and/or adsorbing material 138a via a suitable dispersion method. The suitable and effective odor absorbing, neutralizing, controlling, removing and/or adsorbing material 138a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 138 meets respective state flammability requirements.

A fabric casing 140 sewn together along perimeter sides encloses the structural body 139, and wherein the fabric casing 140 may include a plurality of spatially-oriented pore openings, or small or micro apertures.

The mattress support 130 is manufactured so as to be sized and dimensioned to accommodate single, twin, full, queen, king, California King, Eastern King beds, and the like.

Figure 18A:
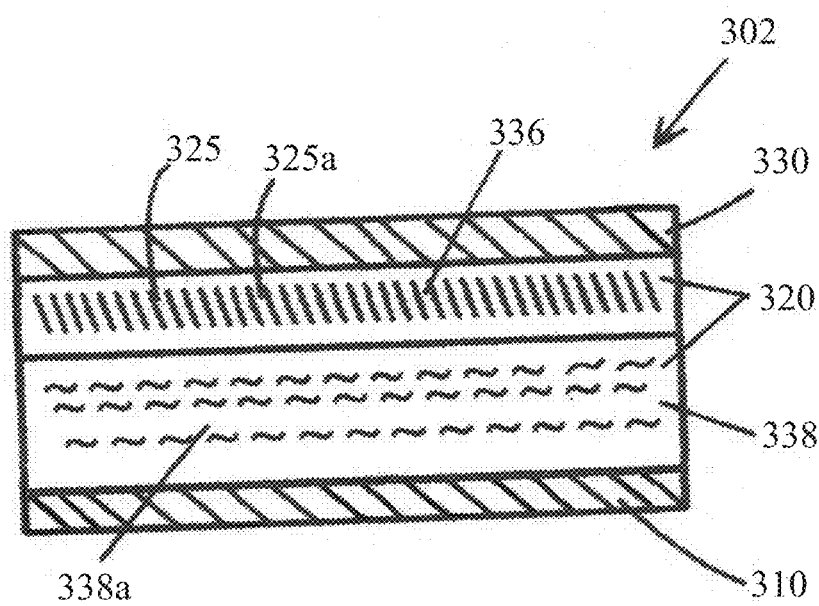
FIG. 18A is a cross-sectional view, on an enlarged scale, of a bedding structure of the sleeping bed device of FIG. 18, in accordance to one embodiment of the present invention.

Referring now more particularly to FIGS. 18 and 18A, in accordance to another embodiment of the present invention, an odor absorbing and controlling sleeping bed device 300 is disclosed. The odor absorbing and controlling sleeping bed device 300, hereinafter "sleeping bed device 300", comprises a bedding structure 302 having a generally rectangular configuration, the bedding structure 302 comprises an outer layer 310, an inner layer 330, and at least one intermediate layer 320 interposed between the outer and inner layers 310 and 330. The layers 310, 320, and 330 are fixedly joined together around the layers' 310, 320, and 330 perimeters by stitching.

The sleeping bed device 300 includes a closure system 340 which retains the device 300 in a folded configuration (sleeping bag or a once folded configuration), as illustrated in FIG. 18. The closure system 340 may include a zipper system 342 (as shown), a snap system, a button system, and a hook-and-loop system (e.g., Velcro® brand fastener). All of these types of closures are known in the art, and with the exception of the zipper system 342, the previously disclosed closures will not be described further.

The zipper system 342 includes zipper slides 344 and 346 extending along and secured by stitching 348 to opposed peripheral side edges of the bedding structure 302, and to the bottom side edge of the bedding structure 302 on opposite sides of a vertical centerline 350, so that when the bedding structure 302 is folded along the centerline 350, the zipper slides 344 and 346 may be joined together by a zipper slider 343.

The outer layer 310 is constructed of a suitable water-resistant textile sheet material 311, such as including, but not limited to Nylon® and Gore-Tex®. The inner layer 330 and is constructed of an insulating material 332 or a material which provides comfort to the user. Insulating materials envisioned for constructing the inner layer include, but are not limited to natural and synthetic textiles (e.g., cotton, wool, polyester, and fleece).

In accordance to one embodiment, the at least one intermediate layer 320 comprises a woven textile material 325. The woven textile material 325 may be further defined as a double woven fabric.

The woven textile material 325 is disposed with an odor absorbing, neutralizing, controlling, removing and/or adsorbing material 325a. In accordance to one embodiment, the woven textile material 325 comprises an odor absorbing, neutralizing, controlling, removing and/or adsorbing material 325a comprising activated charcoal fibers (or "fibres"), thereby forming a double woven activated charcoal fiber (or fibre) cloth 336. For purposes of brevity and obviating redundancy, the woven textile material 325 and double woven activated charcoal fiber cloth 336 is constructed of the same materials, and implements the same construction methods and systems, including features, and advantages associated with, and in accordance to the embodiments as previously described hereinabove concerning the woven textile material 25, 25a, 135, 225 and double woven activated charcoal fiber cloth 26, 26a, 136, 226.

According to another embodiment, the intermediate layer 320 comprises the woven textile material 325 and a foam or cellular polymer, resistant cushion material 338 positioned between the woven textile material 325 and the outer layer 310.

In accordance to one embodiment, the cushion material 338 of intermediate layer 320 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 338 is integrated with a suitable and effective odor absorbing, neutralizing, controlling, removing and/or adsorbing material 338a via a suitable dispersion method. The suitable and effective odor absorbing, neutralizing, controlling, removing and/or adsorbing material 338a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 338 meets respective state flammability requirements.

Figure 19:
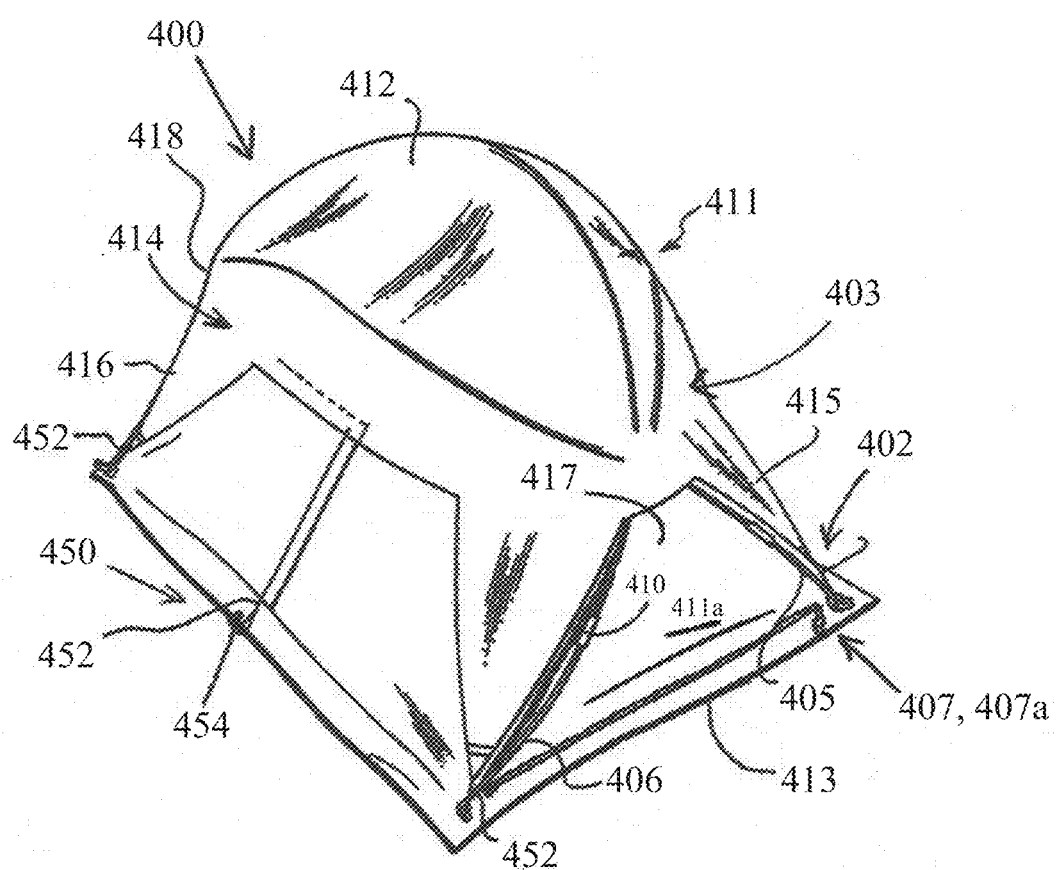
FIG. 19 is a perspective view of an odor absorbing and controlling tent, in accordance to another embodiment of the present invention.

Referring now to FIG. 19, in accordance to still another embodiment of the present invention, an odor absorbing and controlling tent 400 is disclosed. The odor absorbing and controlling tent 400, hereinafter "tent 400", comprises a frame 402 including a plurality of members 404, wherein the plurality of members 404 comprising a plurality of cross members 405, 406 and side members (not shown), the side members having opposed ends detachably secured to lower ends of cross members 405, 406. The plurality of members 404 may include a plurality of rigid, semi-rigid, or flexible sections detachably joined together in end-to-end relationship by couplings 410 in a known manner.

The tent 400 further comprises sheet material 403 fixedly supported by the frame 402 formed into an enclosure 411 having at least one closable opening 411*a*. The enclosure 411 comprises a roof or top wall 412, a floor or bottom wall 413, and a peripheral wall 414 which includes opposing side walls 415, 416 and opposing end walls 417, 418.

The tent 400 may include a closure system 407 for opening and securing the at least one closable opening 411*a* in a closed condition. The closure system 407 may include a zipper system 407*a*, as shown in FIG. 19.

The tent 400 may be anchored to the ground by an anchor assembly 450. The anchor assembly may comprise a plurality of cords 452 and a plurality of stakes 454. The cords 452 are coupled to the peripheral wall 414 and looped around a respective stake 454.

Figure 19A:
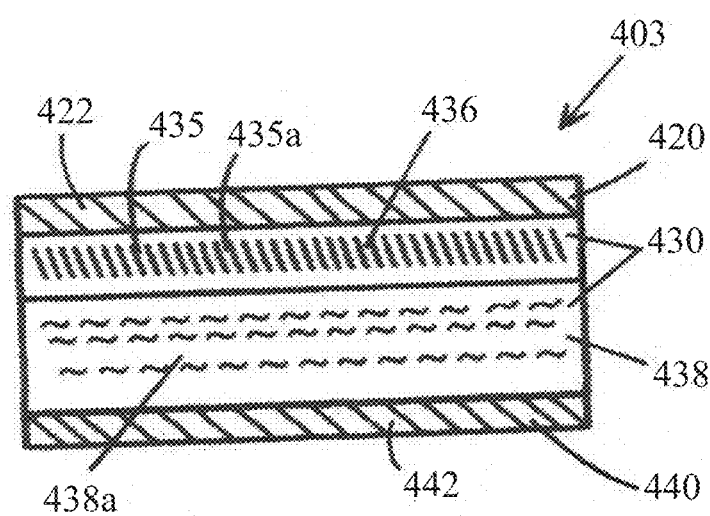
FIG. 19A is a cross-sectional view, on an enlarged scale, of a sheet material of the tent of FIG. 19, in accordance to one embodiment of the present invention.

Referring now more particularly to FIG. 19A, the sheet material 403 of tent 400 comprises an upper layer 420, a lower layer 440, and at least one intermediate layer 430 interposed between the upper and lower layers 420 and 440. The layers 420, 430, and 440, and are fixedly joined together around the layers' 420, 430, and 440 perimeters by stitching.

The upper layer 420 and lower layer 440 are each constructed of an insulating material 422 and 442, respectively, or a material which provides comfort to the user. Insulating materials envisioned for constructing the upper and lower layers 420 and 440 include, but are not limited to natural and synthetic textiles (e.g., cotton, wool, polyester, and fleece).

In accordance to one embodiment, the at least one intermediate layer 430 comprises a woven textile material 435. The woven textile material 435 may be further defined as a double woven fabric.

The woven textile material 435 is disposed with an odor absorbing, neutralizing, controlling, removing and/or adsorbing material 435*a*. In accordance to one embodiment, the woven textile material 435 comprises an odor absorbing, neutralizing, controlling, removing and/or adsorbing material 435*a* comprising activated charcoal fibers (or "fibres"), thereby forming a double woven activated charcoal fiber (or fibre) cloth 436. For purposes of brevity and obviating redundancy, the woven textile material 435 and double woven activated charcoal fiber cloth 436 is constructed of the same materials, and implements the same construction methods and systems, including features, and advantages associated with, and in accordance to the embodiments as previously described hereinabove concerning the woven textile material 25, 25*a*, 135, 225, 325 and double woven activated charcoal fiber cloth 26, 26*a*, 136, 226, 326.

According to another embodiment, the intermediate layer 430 comprises the woven textile material 435 and a foam or cellular polymer, resistant cushion material 438 positioned between the woven textile material 435 and the lower layer 440.

In accordance to one embodiment, the cushion material 438 of intermediate layer 430 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 438 is integrated with a suitable and effective odor absorbing, neutralizing, controlling, removing and/or adsorbing material 438*a* via a suitable dispersion method. The suitable and effective odor absorbing, neutralizing, controlling, removing and/or adsorbing material 438*a* is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 438 meets respective state flammability requirements.

Finally, regarding FIGS. 20-25, in accordance to yet another embodiment of the present invention, an undergarment with odor absorbing and controlling article 500 is disclosed. The undergarment with odor absorbing and controlling article 500, hereinafter "article 500", may be in the form of different styles of undergarments such as men's briefs and boxers, and women's briefs and panties. Consequently, men's and women's undergarments comprise elements being substantially common and consistent with respect to one another.

In particular reference to FIGS. 20-23, according to one embodiment, the article 500 comprises a brief member 501 having a continuous body panel 502, wherein body panel 502 includes a front panel 503 connected to a rear panel 504 by a crotch web 505 or panel. A continuous elastomeric band 506 is affixed to an upper end of the body panel 502, with right and left leg openings 507 and 508, respectively, directed through the body panel 502 between the front and rear panels 503 and 504, respectively. The leg openings 507 and 508 may be reinforced by fabric strips 509 that may be of an elastic or inelastic material.

The crotch web 505 is a piece of material which may be attached by its edges to the front F of the brief member 501, and extends from the elastic band 506 to an area between the leg openings 507 and 508. The crotch web 505 may be attached by simple seams but is preferably attached by double-stitched taping seams 510, which are commonly utilized for constructing men's briefs. The attachment points for the crotch web 505 may be coextensive with the edges of the leg openings 507 and 508, and the taping seams 510 may be of the same type as the fabric strips 509.

A conventional fly means 512 may be provided along the front of brief member 501, between the leg openings 507 and 508.

The brief member 501 is constructed of a material which provides comfort to the user. Such construction materials are envisioned to include natural and synthetic textiles (e.g., cotton, cotton blend, wool, polyester, silk, and fleece).

Figure 24:
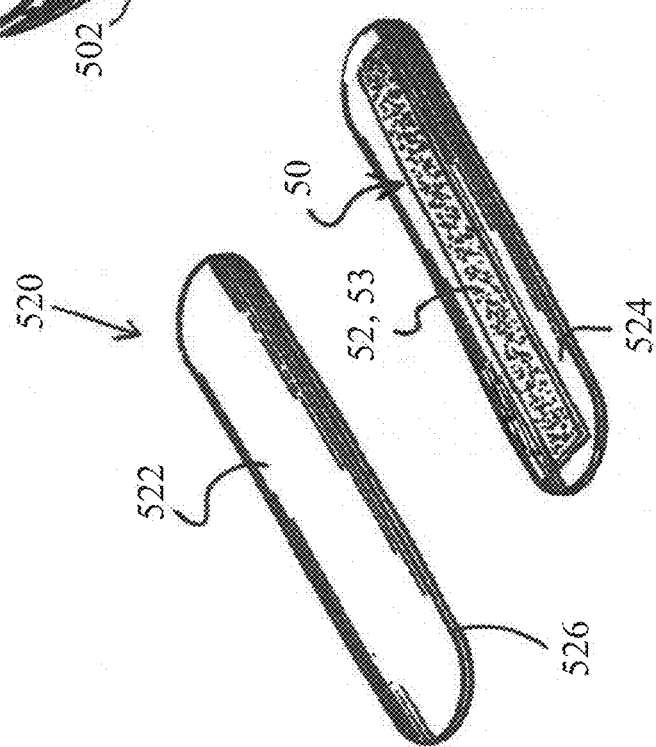
FIG. 24 illustrates a pair of pads, one of which illustrating the upper surface thereof, and the other pad illustrating the lower surface thereof, in accordance to one embodiment of the present invention.
Figure 25:
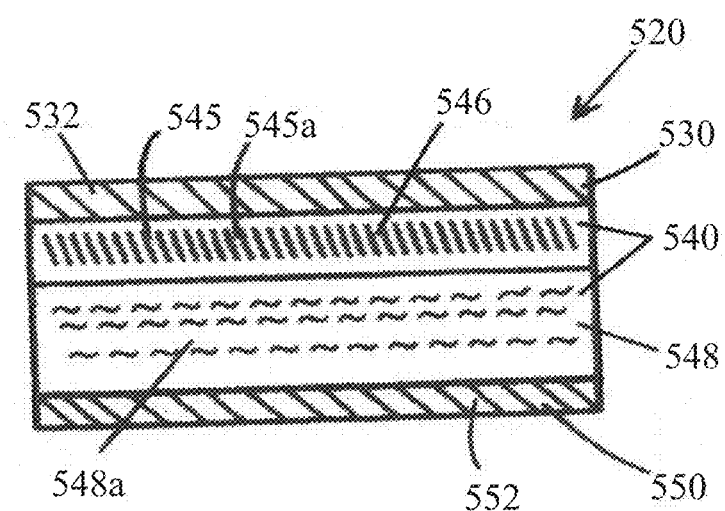
FIG. 25 is a cross-sectional view, on an enlarged scale, of the pad of FIG. 24, in accordance to one embodiment of the present invention.

Referring now more particularly to FIGS. 24 and 25, a pad 520 is disclosed, wherein pad 520 is integrated with an undergarment to absorb, control, remove and/or neutralize malodors associated with flatulence. The pad 520 comprises an elongated, flat, prolate configuration having an upper surface 522 opposing a lower surface 524, and a continuous sidewall 526 integrally joining the upper surface 522 and lower surface 524.

In accordance to one embodiment, the pad 520 is secured to the interior surface of the brief member 501 or panty member 501a by suitable stitching, each consisting of a seam, and wherein each seam may be combined with an overcast protective stitching to provide support to pad 520 so as to possess greater strength.

Figure 22:
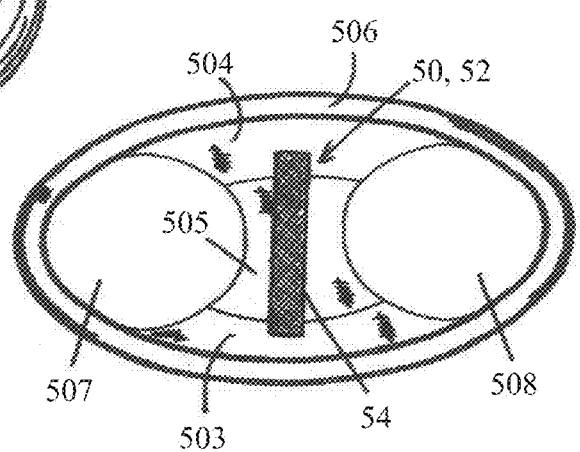
FIG. 22 is a top plan view of an undergarment illustrating one portion of a fastener secured to an interior thereof, the fastener for engaging a complementary fastener portion facilitating releasable attachment of a pad to the undergarment, in accordance to one embodiment of the present invention.
Figure 21A:
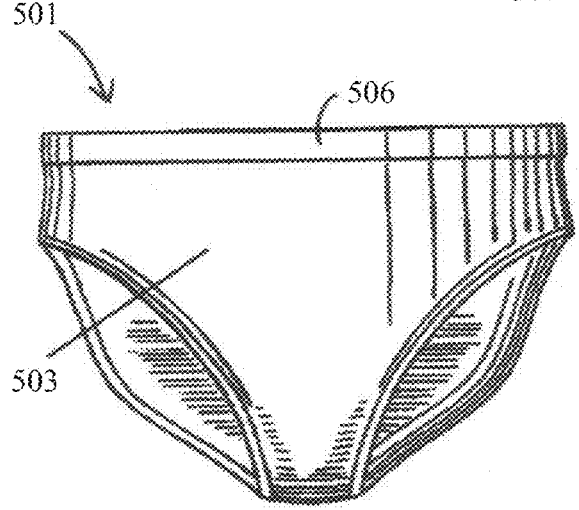
FIG. 21A is a front elevational view of the undergarment of FIG. 21.
Figure 23:
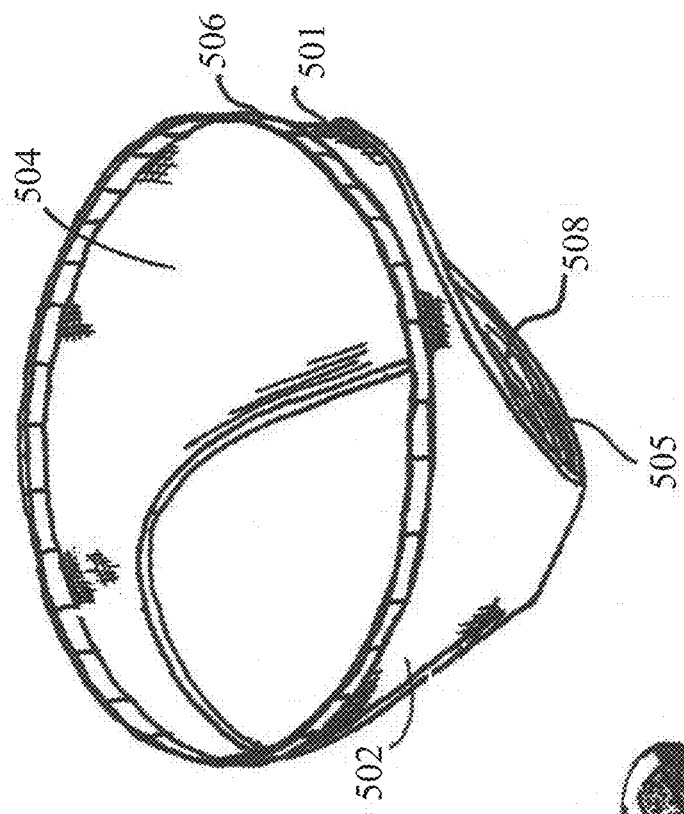
FIG. 23 is a left, partially top front perspective view of an exemplary women's undergarment in the form of a panty.

In reference to FIGS. 22 and 24, in accordance to one embodiment, the pad 520 is releasably attachable to the top panel structure 20 via a fastening means 50, such as a hook-and-loop fastening system 52, namely, the Velcro® brand hook-and-loop fastener. The lower surface 524 of pad 520 is releasably attached to the interior surface of the brief member 501 or panty member 501a. The lower surface 524 of pad 520 comprises a hook-and-loop fastener strip portion 53 secured axially about an elongated centerline thereof. The interior surface of the brief member 501 comprises a complementary hook-and-loop fastener strip portion 54 secured thereto and extending from a portion of the front panel 503, along crotch web 505, and terminating at the rear panel 504. The hook-and-loop fastener strip portion 53 of pad 520 engages the complementary hook-and-loop fastener portion 54 of brief member 501, thereby releasably attaching the pad 520 to the brief member 501. The fastening means 50 may comprise other complementary type or fastening systems which include, but are not limited to, adhesive strips with releasable liners.

Figure 20:
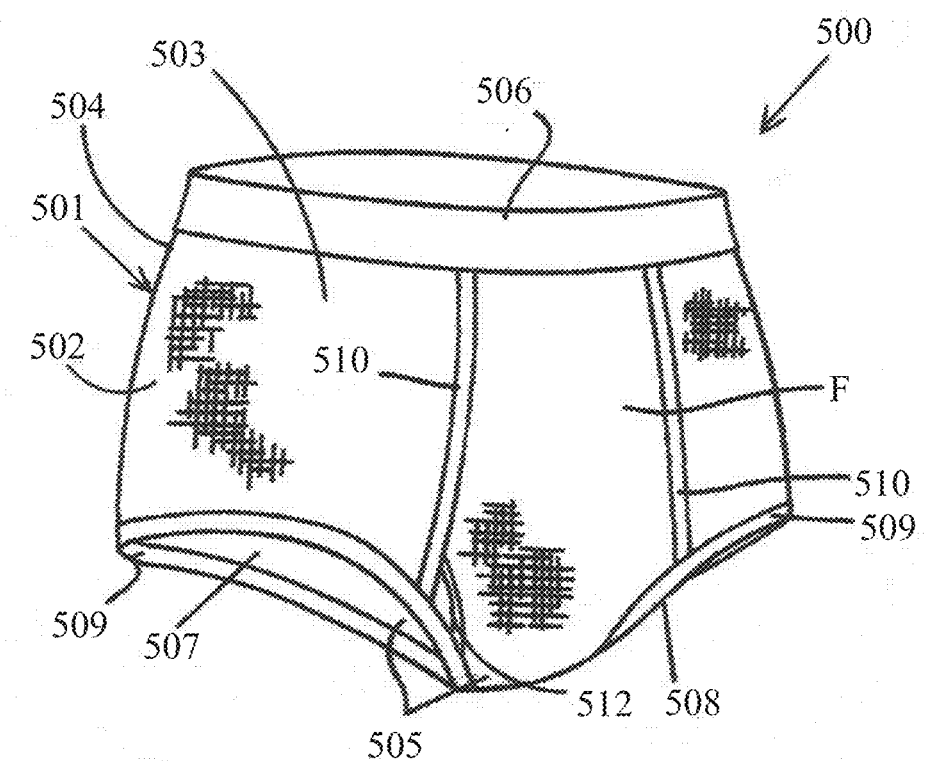
FIG. 20 is a right, front perspective view of an undergarment integrated with an with odor absorbing and controlling article, in accordance to still another embodiment of the present invention.
Figure 20A:
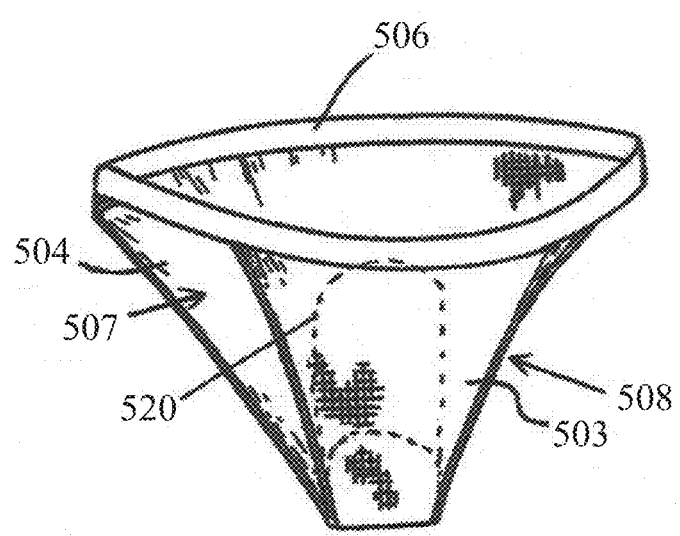
FIG. 20A is a perspective view of an alternative undergarment style integrated with an with odor absorbing and controlling article, in accordance to one embodiment of the present invention.
Figure 21:
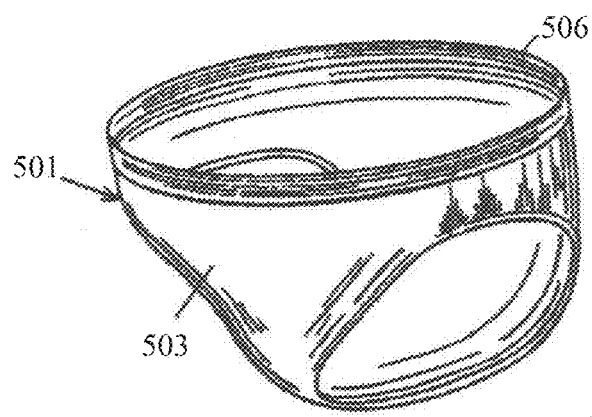
FIG. 21 is a left, partially top front perspective view of an alternative undergarment style integrated with an with odor absorbing and controlling article, in accordance to one embodiment of the present invention.

Referring now more particularly to FIGS. 20A and 25, the pad 520 comprises an upper layer 530, a lower layer 550, and at least one intermediate layer 540 interposed between the upper and lower layers 530 and 550. The layers 530, 540, and 550 are fixedly joined together around the layers' 530, 540, and 550 perimeters by stitching.

The upper layer 530 and lower layer 550 are each constructed of an insulating material 532 and 552, respectively, or a material which provides comfort to the user. Insulating materials envisioned for constructing the upper and lower layers 530 and 550 include, but are not limited to natural and synthetic textiles (e.g., cotton, wool, polyester, and fleece).

In accordance to one embodiment, the at least one intermediate layer 540 comprises a woven textile material 545. The woven textile material 545 may be further defined as a double woven fabric.

The woven textile material 545 is disposed with an odor absorbing, neutralizing, controlling, removing and/or adsorbing material 545a. In accordance to one embodiment, the woven textile material 545 comprises an odor absorbing, neutralizing, controlling, removing and/or adsorbing material 545a comprising activated charcoal fibers (or "fibres"), thereby forming a double woven activated charcoal fiber (or fibre) cloth 546. For purposes of brevity and obviating redundancy, the woven textile material 545 and double woven activated charcoal fiber cloth 546 is constructed of the same materials, and implements the same construction methods and systems, including features, and advantages associated with, and in accordance to the embodiments as previously described hereinabove concerning the woven textile material 25, 25a, 135, 225 and double woven activated charcoal fiber cloth 26, 26a, 136, 226.

According to another embodiment, the intermediate layer 540 comprises the woven textile material 545 and a foam or cellular polymer, resistant cushion material 548 positioned between the woven textile material 545 and the lower layer 550.

In accordance to one embodiment, the cushion material 548 of intermediate layer 540 is constructed of a polymer material, particularly a polymer foam material, and preferably selected from the group which includes, but is not limited to polyurethane, and polyisocyanurate. Other suitable polymer foam materials include polyolefins, polyvinylchloride, alkenyl aromatic polymers, cellulosic polymers, polycarbonates, polyetherimides, polyamides, polyesters, polyvinylidene chloride, polymethylmethacrylate, polyurethanes, polyisocyanurates, phenolics, copolymers and terpolymers of the foregoing, polymer blends, rubber modified polymers, and the like. Suitable polyolefins include polyethylene and polypropylene.

In accordance to one embodiment, the selected polymer foam construction material 548 is integrated with a suitable and effective odor absorbing, neutralizing, controlling, removing and/or adsorbing material 548a via a suitable dispersion method. The suitable and effective odor absorbing, neutralizing, controlling, removing and/or adsorbing material 548a is preferably an activated carbon or activated charcoal.

Other suitable and effective odor absorbing, neutralizing, controlling, removing and/or adsorbing materials may be utilized for incorporation with the selected polymer foam construction material, wherein said other suitable and effective materials include, but are not limited to, clays, baking soda (sodium bicarbonate), diatomaceous earths, activated alumina, and zeolites. These other suitable and effective odor absorbing, neutralizing, controlling, removing and/or adsorbing materials can be used alone or in combination.

In addition, the selected polymer foam construction material 548 meets respective state flammability requirements.

It is envisioned that the various embodiments, as separately disclosed, are interchangeable in various aspects, so that elements of one embodiment may be incorporated into one or more of the other embodiments, and that specific positioning of individual elements may necessitate other arrangements not specifically disclosed to accommodate performance requirements or spatial considerations.

It is to be understood that the embodiments and claims are not limited in its application to the details of construction and arrangement of the components set forth in the description and illustrated in the drawings. Rather, the description and the drawings provide examples of the embodiments envisioned, but the claims are limited to the specific embodiments. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the U.S. Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. An odor control article, the article comprises:
    a panel structure, the panel structure comprises a top opposing a bottom, and a continuous, upwardly-extending sidewall integrally joining the top and the bottom, the top comprises a woven textile material, the woven textile material comprises an odor control material, wherein the odor control material comprises activated charcoal fibers forming a double woven activated charcoal cloth;
    a fabric casing, the fabric casing envelopes the woven textile material; and
    a holding component detachably secured to the panel structure or the fabric casing.

2. An odor control device, the device comprises:
    a panel structure, the panel structure comprises:
        an upper layer, the upper layer comprises a woven textile material, wherein the woven textile material of the upper layer comprises an odor control material, wherein the odor control material comprises activated charcoal fibers forming a double woven activated charcoal fiber cloth; and
        a lower layer, the lower layer comprises a cellular polymer, resistant cushion material, the upper layer is suitably affixed to the lower layer, and wherein the upper layer and the lower layer jointly form a structural body;
    a fabric cover, the fabric cover encloses the panel structure forming an odor control article, the odor control article comprises a top opposing a bottom, and a continuous, upwardly-extending sidewall integrally joining the top and the bottom; and
    an adjustable holding component detachably secured to the panel structure or the fabric cover.

3. The odor control device of claim 2, wherein the cellular polymer, resistant cushion material of the lower layer is integrated dispersedly with an odor control material, the odor control material of the cellular polymer, resistant cushion material comprises at least one of an odor absorbing material, an odor neutralizing material, an odor removing material, and an odor adsorbing material.

4. The odor control device of claim 3, wherein the odor control material of the cellular polymer, resistant cushion material comprises activated carbon or activated charcoal.

5. The odor control device of claim 2, wherein the adjustable holding component is detachably secured to the fabric cover or the panel structure via an attachment mechanism.

6. The odor control device of claim 5, wherein the adjustable holding component comprises an adjustable elongated strap constructed of a lightweight, flexible material, the strap includes a first free end and a second free end.

7. The odor control device of claim 6, wherein the strap comprises a length suitable for supporting the fabric cover or the panel structure in a suspended manner from a shoulder or shoulders of a user, thereby providing a shoulder strap.

8. The odor control device of claim 5, wherein the attachment mechanism comprises complementary couplers affixed to the first and second free ends of the strap and to at least two sections of the continuous sidewall of the odor control article.

9. The odor control device of claim 8, wherein the complementary couplers comprise hook-and-loop fasteners.

10. The odor control device of claim 8, wherein the complementary couplers comprise at least two D-rings.

11. The odor control device of claim 7, wherein the strap is adjusted to a selectively-desired shorter length and fixed at the desired shortened length to provide a handle.

12. The odor control device of claim 11, further comprising an auxiliary strap.

13. The odor control device of claim 12, wherein the auxiliary strap detachably secures sections of the handle in a compressed and bound condition.

* * * * *